(12) United States Patent
Ståhle-Bäckdahl et al.

(10) Patent No.: US 8,936,807 B2
(45) Date of Patent: *Jan. 20, 2015

(54) USE OF THE CATHELICIDIN LL-37 AND DERIVATIVES THEREOF FOR WOUND HEALING

(71) Applicant: Lipopeptide AB, Solna (SE)

(72) Inventors: Mona Ståhle-Bäckdahl, Stockholm (SE); Johan Heilborn, Stockholm (SE); Anders Carlsson, Stockholm (SE); Conny Bogentoft, Hässelby (SE)

(73) Assignee: Lipopeptide AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/938,120

(22) Filed: Jul. 9, 2013

(65) Prior Publication Data

US 2013/0287839 A1    Oct. 31, 2013

Related U.S. Application Data

(62) Division of application No. 13/193,131, filed on Jul. 28, 2011, now Pat. No. 8,506,994, which is a division of application No. 12/232,215, filed on Sep. 12, 2008, now Pat. No. 8,012,933, which is a division of application No. 10/543,659, filed as application No. PCT/SE2004/000111 on Jan. 28, 2004, now Pat. No. 7,452,864.

(60) Provisional application No. 60/444,964, filed on Feb. 5, 2003.

(30) Foreign Application Priority Data

Jan. 29, 2003   (SE) ...................... 0300207

(51) Int. Cl.
| | |
|---|---|
| C07K 14/47 | (2006.01) |
| A61K 9/127 | (2006.01) |
| A61K 38/16 | (2006.01) |
| C12N 5/00 | (2006.01) |
| C12N 5/071 | (2010.01) |

(52) U.S. Cl.
CPC .............. *C07K 14/47* (2013.01); *A61K 9/1272* (2013.01); *A61K 38/16* (2013.01); *C07K 14/4723* (2013.01); *C12N 5/0018* (2013.01); *C12N 5/0629* (2013.01); *C12N 2500/32* (2013.01); *C12N 2500/36* (2013.01); *Y10S 514/938* (2013.01)
USPC .......... 424/450; 530/324; 514/23; 424/93.21; 435/404; 514/938

(58) Field of Classification Search
CPC ......................... A61K 38/00; C07K 14/4723
See application file for complete search history.

(56) References Cited

U.S. PATENT DOCUMENTS

| 5,925,534 A | 7/1999 | Miki et al. |
|---|---|---|
| 6,255,282 B1 | 7/2001 | Jaynes |
| 7,452,864 B2 * | 11/2008 | Stahle-Backdahl et al. ... 514/1.1 |
| 7,591,997 B2 | 9/2009 | Boman et al. |
| 2002/0072495 A1 | 6/2002 | Chertov et al. |
| 2002/0169279 A1 * | 11/2002 | Montelaro et al. ............ 530/324 |
| 2003/0022829 A1 | 1/2003 | Maury et al. |

FOREIGN PATENT DOCUMENTS

| EP | 0 935 965 A1 | 8/1999 |
|---|---|---|
| EP | 1 358 888 A1 | 11/2003 |
| WO | WO 95/20943 A1 | 8/1995 |
| WO | WO 95/20944 A1 | 8/1995 |
| WO | WO 95/20945 A1 | 8/1995 |
| WO | WO 96/08508 A1 | 3/1996 |
| WO | WO 96/09322 A2 | 3/1996 |
| WO | WO 99/44586 A1 | 9/1999 |
| WO | WO 00/57895 A1 | 10/2000 |
| WO | WO 02/06821 A2 | 1/2002 |
| WO | WO 02/09507 A1 | 2/2002 |
| WO | WO 02/095076 A2 | 11/2002 |
| WO | WO 2004/056307 A2 | 7/2004 |

OTHER PUBLICATIONS

Johansson et al. (J. Biol. Chem. 1998; 273: 3718-3724).*
Bioke et al. (Cleveland Clinic Center for Continuing Education publications: Disease Management Project. Prevention and Treatment of Leg and Foot Ulcers in Diabetes Mellitus. 2010; pp. 1-9).*
Heilborn et al., "The Antimicrobial Peptide LL-37 is Required for Re-Epithelialization of Human Skin Wounds and is Lacking in Chronic Ulcers," Journal of Investigative Dermatology (2002), Abstract 117.
Agerberth et al., "FALL-39, a Putative Human Peptide Antibiotic, Is Cysteine-free and Expressed in Bone Marrow and Testis," Proc. Natl. Acad. Science, USA (1995), vol. 92, pp. 195-199.
Auxenfans et al., "Use of Allogenic Epidermal Sheets for Difficult Wound Healing: Selection and Testing of Relevant Growth Factors," Bio-Medical Materials and Engineering (2006), vol. 16, pp. S73-S83.
Bals, R., "Epithelial Antimicrobial Peptides in Host Defense Against Infection," Respiratory Research (2000), vol. 1, No. 3, pp. 141-150.
Boukamp et al., "Normal Keratinization in a Spontaneously Immortalized Aneuploid Human Keratinocyte Cell Line," Journal of Cell Biology (1988), vol. 106, pp. 761-771.
Braff et al., "Structure-Function Relationships Among Human Cathelicidin Peptides: Dissociation of Antimicrobial Properties from Host Immunostimulatory Activities," Journal of Immunology (2005), vol. 174, pp. 4271-4278.
Canadian Office Action dated Oct. 27, 2011 for Application No. 2,513,598.
Carretero et al., "In Vitro and in Vivo Wound Healing-Promoting Activities of Human Cathelicidin LL-37," Journal of Investigative Dermatology (2008), vol. 128, pp. 223-236, published online Sep. 13, 2007.

(Continued)

*Primary Examiner* — Scott Long
(74) *Attorney, Agent, or Firm* — McCarter & English, LLP; Steven G. Davis

(57) ABSTRACT

Use of the antimicrobial cathelicidin peptide II-37, N-terminal fragments of LL-37 or extended sequences of LL-37 having 1-3 amino acids in the C-terminal end, for stimulating proliferation of epithelial and stromal cells and thereby healing of wounds, such as chronic ulcers. The cytotoxic effect of LL-37 may be reduced by including a bilayer-forming polar lipid, especially a digalactosyldiacylglycerol, in pharmaceutical compositions and growth media comprising LL-37.

2 Claims, 4 Drawing Sheets

(56) References Cited

OTHER PUBLICATIONS

Chen et al., "Synthetic Magainin Analogues with Improved Antimicrobial Activity," FEBS Letters (1988), vol. 236, No. 2, pp. 462-466.
Cohen, S., "The Stimulation of Epidermal Proliferation by a Specific Protein (EGF)," Developmental Biology (1965), vol. 12, pp. 394-407.
Cook et al., "Viability Measurements in Mammalian Cell Systems," Analytical Biochemistry (1989), vol. 179, pp. 1-7.
Cowland et al., "hCAP-18, a Cathelin/pro-bactenecin-like Protein of Human Neutrophil Specific Granules," FEBS Letters (1995), vol. 368, pp. 173-176.
Del Rio et al., "A Preclinical Model for the Analysis of Genetically Modified Human Skin In Vivo," Hum. Gene Ther. (2002), vol. 13, pp. 959-968.
Dorschner et al., "Cutaneous Injury Induces the Release of Cathelicidin Anti-Microbial Peptides Active Against Group A *Streptococcus*," J. Invest. Dermatol. (2001), vol. 117, pp. 91-97.
Fields et al., "Solid Phase Peptide Synthesis Utilizing 9-fluorenylmthoxycarbonyl Amino Acids," Int. J. Peptide Protein Res. (1990), vol. 35, pp. 161-214.
Froget et al., "Wound Healing Mediator Production by Human Dermal Fibroblasts Grown Within a Collagen-GAG Matrix for Skin Repair in Humans," European Cytokine Network (2003), vol. 14, No. 1, pp. 60-64.
Frohm et al., "The Expression of the Gene Coding of the Antibacterial Peptide LL-37 is Induced in Human Keratinocytes during Inflammatory Disorders," Journal of Biological Chemistry (1997), vol. 272, No. 24, pp. 15258-63.
Gallo et al., "Syndecans, Cell Surface Heparan Sulfate Proteoglycans, Are Induced by a Proline-rich Antimicrobial Peptide from Wounds," Proc. Natl. Acad. Sci. USA (1994), vol. 91, pp. 11035-11039.
Giangaspero et al., "Amphipathic a Helical Antimicrobial Peptides: A Systematic Study of the Effects of Structural and Physical Properties on Biological Activity," Eur. J. Biochem. (2001), vol. 268, pp. 5589-5600.
Gillitzer et al., "Chemokines in Cutaneous Wound Healing," Journal of Leukocyte Biology (2001), vol. 69, pp. 513-521.
Green et al., "Growth of Cultured Human Epidermal Cells into Multiple Epithelia Suitable for Grafting," Proc. Natl. Acad. Science, USA (1979), vol. 76, No. 11, pp. 5665-5668.
Gronberg, "Declaration of Doctor Alvar Gronberg," Feb. 18, 2008, including Annex A, "Description of Results From an Experiment."
Gudmundsson et al., "The Human Gene FALL39 and Processing of the Cathelin Precursor to the Antibacterial Peptide LL-37 in Granulocytes," Eur. J. Biochem. (1996), vol. 238, pp. 325-332.
Gutsmann et al., Interaction of CAP18-Derived Peptides with Membranes Made from Endotoxins or Phospholipids, Biophysical Journal (2001), vol. 80, pp. 2935-2945.
Hecht, G., "Innate Mechanisms of Epithelial Host Defense: Spotlight on Intestine," Am. J. Physiol. Cell Physiol. (1999), vol. 277, pp. 351-358.
Hehenberger et al., "High Glucose-induced Growth Factor Resistance in Human Fibroblasts Can Be Reversed by Antioxidants and Protein Kinase C-Inhibitors," Cell Biochemistry and Function (1997), vol. 15, pp. 197-201.
Heilborn et al., "The Cathelicidin Anti-Microbial Peptide LL-37 is Involved . . . ," J. Invest. Dermatol. (2003), vol. 120, pp. 379-389.
Inoue et al., "Collagenase Expression Is Rapidly Induced in Wound-edge Keratinocytes after Acute Injury in Human Skin, Persists During Healing, and Stops at Re-Epithelialization," J. Invest. Dermatol. (1995) vol. 104, pp. 479-481.
International Preliminary Report on Patentability for PCT Application No. PCT/SE2004/000111, dated Apr. 25, 2005, received May 19, 2005.
International Search Report for PCT Application No. PCT/JP2002/04800, dated Jun. 6, 2003.
International Search Report for PCT Application No. PCT/SE2004/000111, dated Apr. 30, 2004.
Johansson et al., "Conformation-dependent Antibacterial Activity of the Naturally Occurring Human Peptide LL-37," J. of Biol. Chemistry (1998), vol. 273, No. 6, pp. 3718-3724.
Koczulla et al., "An Angiogenic Role for the Human Peptide Antibiotic LL-37/hCAP-18," Journal of Clinical Investigation (2003), vol. 111, No. 11, pp. 1665-1672.
Kratz et al., "Insulin Like Growth Factor-1 and -2 and Their Role in the Re-epithelialisation of Wounds: Interactions With Insulin Like Growth Factor Binding Protein Type 1," Scand. J. Plast. Reconstr. Hand Surg. (1994), vol. 28, pp. 107-112.
Kratz, "Modeling of Wound Healing Processes in Human Skin Using Tissue Culture," Microscopy Research and Technique (1998), vol. 42, pp. 345-350.
Larrick et al., "Antimicrobal Activity of Rabbit CAP18-Derived Peptides," Antimicrobal Agents and Chemotherapy (1993), vol. 37, No. 12, pp. 2534-2539.
Larrick et al., "Anti-microbial Activity of Human CAP18 Peptides," Immunotechnology (1995), vol. 1, pp. 65-72.
Larrick et al., "Human CAP18: a Novel Antimicrobial Lipopolysaccharide-Binding Protein," Infection and Immunity (1995), vol. 63, No. 4, pp. 1291-1297.
Larrick et al., "Structural, Functional Analysis and Localization of the Human CAP18 Gene," FEBS Letters (1996), vol. 398, pp. 74-80.
Lu et al., "Fluorescence Imaging of Reepithelization from Skin Explant Cultures on Acellular Dermis," Wound Repair and Regeneration (2004), vol. 12, pp. 575-586.
Murakami et al., "Postsecretory Processing Generates Multiple Cathelicidins for Enhanced Topical Antimicrobial Defense," Journal of Immunology (2004), vol. 172, pp. 3070-3077.
Neville et al., "Lipid Headgroup Discrimination by Antimicrobial Peptide LL-37: Insight into Mechanism of Action," Biophysical Journal (2006), vol. 90, pp. 1275-1287.
Nilsson et al., "The Human Cationic Antimicrobial Protein (hCAP18), a Peptide Antibiotic, Is Widely Expressed in Human Squamous Epithelia and Colocalizes with Interleukin-6," Infection and Immunity (1999), vol. 67, No. 5, pp. 2561-2566.
Nilsson, M.F., "The Human Antimicrobial Peptide hCAP18 in Epithelial Defense," Nilsson PhD Thesis (2001), Department of Dermatology, Karolinska Hospital, Karolinska Institutet, Stockholm, Sweden (abstract only).
Nilsson, M.F., "The Human Antimicrobial Peptide hCAP18 in Epithelial Defense," Nilsson PhD Thesis (2001), Department of Dermatology, Karolinska Hospital, Karolinska Institutet, Stockholm, Sweden, pp. 43-45.
Oren et al., "Structure and Organization of the Human Antimicrobial Peptide LL-37 in Phospholipid Membranes: Relevance to the Molecular Basis for its Non-cell-selective Activity," Biochemical Journal (1999), vol. 341, pp. 501-513.
Pestonjamasp et al., "Antimicrobial Peptides Are Effectors of Wound Repair," Wound Repair and Regeneration (2001), vol. 9, No. 2, p. 158.
Ramesh et al., "A New Role for Vitamin D: Cholecalciferol Promotes Dermal Wound Strength and Re-epithelization," Indian J. of Experimental Biol. (1993), vol. 31, pp. 778-779.
Rennekampff et al., "Bioactive Interleukin-8 Is Expressed in Wounds and Enhances Wound Healing," Journal of Surgical Research (2000), vol. 93, pp. 41-54.
Resnitzky et al., "Acceleration of the G1/S Phase Transition by Expression of Cyclins D1 and E with an Inducible System," Molecular and Cellular Biology (1994), vol. 14, No. 3, pp. 1669-1679.
Saiman et al., "Cathelicidin Peptides Inhibit Multiply Antibiotic-Resistant Pathogens from Patients with Cystic Fybrosis," Antimicrobial Agents and Chemotherapy (2001), vol. 45, No. 10, pp. 2838-2844.
Scharffetter-Kochanek et al., "Cellular and Molecular Mechanisms of Tissue Repair," Basic Res. Cardiol. (1998), vol. 93, Suppl. 3, pp. 1-3.
Selsted et al., "Primary Structures of MCP-1 and MCP-2, Natural Peptide Antibiotics of Rabbit Lung Macrophages," Journal of Biological Chemistry (1983), vol. 258, No. 123, pp. 14485-14489.
Sorensen et al., "Human Cathelicidin, hCAP-18, Is Processed to the Antimicrobial Peptide LL-37 by Extracellular Cleavage With

(56) References Cited

OTHER PUBLICATIONS

Proteinase 3," Blood (2001), vol. 97, No. 12, pp. 3951-3959, published online (www.bloodjournal.org) Jun. 26, 2009 and Aug. 13, 2009.

Sorensen et al., "The Human Antibacterial Cathelicidin, hCAP-18, Is Bound to Lipoproteins in Plasma," Journal of Biochemistry (1999), vol. 274, No. 32, pp. 22445-22451.

Sorensen et al., "The Human Antibacterial Cathelicidin, hCAP-18, Is Synthesized in Myelocytes and Metamyeloctyes and Localized to Specific Granules in Neutrophils," Blood (1997), vol. 90, No. 7, pp. 2796-2803.

Steinstraesser et al., "Host Defense Peptides in Wound Healing," Mol. Med. (2008), vol. 14, Nos. 7-8, pp. 528-537.

Turner et al., "Activities of LL-37, a Cathelin-Associated Antimicrobial Peptide of Human Neutrophils," Antimicrobial Agents and Chemotherapy (1998), vol. 42, No. 9, pp. 2206-2214.

Wang et al., "Apolipoprotein A-I Binds and Inhibits the Human Antibacterial/Cytotoxic Peptide LL-37," Journal of Biological Chemistry (1998), vol. 273, No. 50, pp. 33115-33118.

Yamasaki et al., "Increased Serine Protease Activity and Cathelicidin Promotes Skin Inflammation in Rosacea," Nature Medicine (2007), vol. 13, No. 8, pp. 975-980.

Yatomi et al., "Sphingosine 1-phosphate as a Major Bioactive Lysophospholipid . . . ," Blood (2000), vol. 96, No. 10, pp. 3431-3438.

Yeaman et al., "Mechanisms of Antimicrobial Peptide Action and Resistance," Pharmacol. Rev. (2003), vol. 55, No. 1, pp. 27-55.

Zasloff, M., "Antimicrobial Peptides of Multicellular Organisms," Nature (2002), vol. 415, pp. 389-395.

Zhang et al., "The Membrane-bound Structure and Topology of a Human α-Defensin Indicate a Dimer Pore Mechanism for Membrane Disruption," Biochemistry (2010), vol. 49, No. 45, pp. 9770-9782 (abstract only).

\* cited by examiner

The vector pIRES2-EGFP including the coding sequence for hCAP18

```
TAGTTATTAA TAGTAATCAA TTACGGGGTC ATTAGTTCAT AGCCCATATA
TGGAGTTCCG CGTTACATAA CTTACGGTAA ATGGCCCGCC TGGCTGACCG
CCCAACGACC CCCGCCCATT GACGTCAATA ATGACGTATG TTCCCATAGT
AACGCCAATA GGGACTTTCC ATTGACGTCA ATGGGTGGAG TATTTACGGT
AAACTGCCCA CTTGGCAGTA CATCAAGTGT ATCATATGCC AAGTACGCCC
CCTATTGACG TCAATGACGG TAAATGGCCC GCCTGGCATT ATGCCCAGTA
CATGACCTTA TGGGACTTTC CTACTTGGCA GTACATCTAC GTATTAGTCA
TCGCTATTAC CATGGTGATG CGGTTTTGGC AGTACATCAA TGGGCGTGGA
TAGCGGTTTG ACTCACGGGG ATTTCCAAGT CTCCACCCCA TTGACGTCAA
TGGGAGTTTG TTTTGGCACC AAAATCAACG GGACTTTCCA AAATGTCGTA
ACAACTCCGC CCCATTGACG CAAATGGGCG GTAGGCGTGT ACGGTGGGAG
GTCTATATAA GCAGAGCTGG TTTAGTGAAC CGTCAGATCC GCTAGCGCTA
CCGGACTCAG ATCTCGAGCT CAAGCTTCGA ATTCTGCAGT CGACGGTACC
GCGGGCCCTA GAGGGAGGCA GACATGGGGA CCATGAAGAC CCAAAGGGAT
GGCCACTCCC TGGGGCGGTG GTCACTGGTG CTCCTGCTGC TGGGCCTGGT
GATGCCTCTG GCCATCATTG CCCAGGTCCT CAGCTACAAG GAAGCTGTGC
TTCGTGCTAT AGATGGCATC AACCAGCGGT CCTCGGATGC TAACCTCTAC
CGCCTCCTGG ACCTGGACCC CAGGCCCACG ATGGATGGNG ACCCAGACAC
GCCAAAGCCT GTGAGCTTCA CAGTGAAGGA GACAGTGTGC CCCAGGACGA
CACAGCAGTC ACCAGAGGAT TGTGACTTCA AGAAGGACGG GCTGGTGAAG
CGGTGTATGG GGACAGTGAC CCTCAACCAG GCCAGGGGCT CCTTTGACAT
CAGTTGTGAT AAGGATAACA AGAGATTTGC CCTGCTGGGT GATTTCTTCC
GGAAATCTAA AGAGAAGATT GGCAAAGAGT TTAAAAGAAT TGTCCAGAGA
ATCAAGGATT TTTTGCGGAA TCTTGTACCC AGGACAGAGT CCTAGGGATC
CGCCCCTCTC CCTCCCCCCC CCTAACGTT ACTGGCCGAA GCCGCTTGGA
ATAAGGCCGG TGTGCGTTTG TCTATATGTT ATTTTCCACC ATATTGCCGT
CTTTTGGCAA TGTGAGGGCC CGGAAACCTG GCCCTGTCTT CTTGACGAGC
ATTCCTAGGG GTCTTTCCCC TCTCGCCAAA GGAATGCAAG GTCTGTTGAA
TGTCGTGAAG GAAGCAGTTC CTCTGGAAGC TTCTTGAAGA CAAACAACGT
CTGTAGCGAC CCTTTGCAGG CAGCGGAACC CCCCACCTGG CGACAGGTGC
CTCTGCGGCC AAAAGCCACG TGTATAAGAT ACACCTGCAA AGGCGGCACA
ACCCCAGTGC CACGTTGTGA GTTGGATAGT TGTGGAAAGA GTCAAATGGC
TCTCCTCAAG CGTATTCAAC AAGGGGCTGA AGGATGCCCA GAAGGTACCC
CATTGTATGG GATCTGATCT GGGGCCTCGG TGCACATGCT TTACATGTGT
TTAGTCGAGG TTAAAAAAAC GTCTAGGCCC CCCGAACCAC GGGGACGTGG
TTTTCCTTTG AAAAACACGA TGATAATATG GCCACAACCA TGGTGAGCAA
GGGCGAGGAG CTGTTCACCG GGGTGGTGCC CATCCTGGTC GAGCTGGACG
GCGACGTAAA CGGCCACAAG TTCAGCGTGT CCGGCGAGGG CGAGGGCGAT
GCCACCTACG GCAAGCTGAC CCTGAAGTTC ATCTGCACCA CCGGCAAGCT
GCCCGTGCCC TGGCCCACCC TCGTGACCAC CCTGACCTAC GGCGTGCAGT
GCTTCAGCCG CTACCCCGAC CACATGAAGC AGCACGACTT CTTCAAGTCC
GCCATGCCCG AAGGCTACGT CCAGGAGCGC ACCATCTTCT TCAAGGACGA
CGGCAACTAC AAGACCCGCG CCGAGGTGAA GTTCGAGGGC GACACCCTGG
TGAACCGCAT CGAGCTGAAG GGCATCGACT TCAAGGAGGA CGGCAACATC
```
(cont. in Fig. 3B)

FIGURE 3A (cont. from Fig. 3A)
CTGGGGCACA AGCTGGAGTA CAACTACAAC AGCCACAACG TCTATATCAT
GGCCGACAAG CAGAAGAACG GCATCAAGGT GAACTTCAAG ATCCGCCACA
ACATCGAGGA CGGCAGCGTG CAGCTCGCCG ACCACTACCA GCAGAACACC
CCCATCGGCG ACGGCCCCGT GCTGCTGCCC GACAACCACT ACCTGAGCAC
CCAGTCCGCC CTGAGCAAAG ACCCCAACGA GAAGCGCGAT CACATGGTCC
TGCTGGAGTT CGTGACCGCC GCCGGGATCA CTCTCGGCAT GGACGAGCTG
TACAAGTAAA GCGGCCGCGA CTCTAGATCA TAATCAGCCA TACCACATTT
GTAGAGGTTT TACTTGCTTT AAAAAACCTC CCACACCTCC CCCTGAACCT
GAAACATAAA ATGAATGCAA TTGTTGTTGT TAACTTGTTT ATTGCAGCTT
ATAATGGTTA CAAATAAAGC AATAGCATCA CAAATTTCAC AAATAAAGCA
TTTTTTTCAC TGCATTCTAG TTGTGGTTTG TCCAAACTCA TCAATGTATC
TTAAGGCGTA AATTGTAAGC GTTAATATTT TGTTAAAATT CGCGTTAAAT
TTTTGTTAAA TCAGCTCATT TTTTAACCAA TAGGCCGAAA TCGGCAAAAT
CCCTTATAAA TCAAAAGAAT AGACCGAGAT AGGGTTGAGT GTTGTTCCAG
TTTGGAACAA GAGTCCACTA TTAAAGAACG TGGACTCCAA CGTCAAAGGG
CGAAAAACCG TCTATCAGGG CGATGGCCCA CTACGTGAAC CATCACCCTA
ATCAAGTTTT TTGGGGTCGA GGTGCCGTAA AGCACTAAAT CGGAACCCTA
AAGGGAGCCC CCGATTTAGA GCTTGACGGG GAAAGCCGGC GAACGTGGCG
AGAAAGGAAG GGAAGAAAGC GAAAGGAGCG GCGCTAGGG CGCTGGCAAG
TGTAGCGGTC ACGCTGCGCG TAACCACCAC ACCCGCCGCG CTTAATGCGC
CGCTACAGGG CGCGTCAGGT GGCACTTTTC GGGGAAATGT GCGCGGAACC
CCTATTTGTT TATTTTTCTA AATACATTCA AATATGTATC CGCTCATGAG
ACAATAACCC TGATAAATGC TTCAATAATA TTGAAAAAGG AAGAGTCCTG
AGGCGGAAAG AACCAGCTGT GGAATGTGTG TCAGTTAGGG TGTGGAAAGT
CCCCAGGCTC CCCAGCAGGC AGAAGTATGC AAAGCATGCA TCTCAATTAG
TCAGCAACCA GGTGTGGAAA GTCCCCAGGC TCCCCAGCAG GCAGAAGTAT
GCAAAGCATG CATCTCAATT AGTCAGCAAC CATAGTCCCG CCCCTAACTC
CGCCCATCCC GCCCCTAACT CCGCCCAGTT CCGCCCATTC TCCGCCCCAT
GGCTGACTAA TTTTTTTTAT TTATGCAGAG GCCGAGGCCG CCTCGGCCTC
TGAGCTATTC CAGAAGTAGT GAGGAGGCTT TTTTGGAGGC CTAGGCTTTT
GCAAAGATCG ATCAAGAGAC AGGATGAGGA TCGTTTCGCA TGATTGAACA
AGATGGATTG CACGCAGGTT CTCCGGCCGC TTGGGTGGAG AGGCTATTCG
GCTATGACTG GGCACAACAG ACAATCGGCT GCTCTGATGC CGCCGTGTTC
CGGCTGTCAG CGCAGGGGCG CCCGGTTCTT TTTGTCAAGA CCGACCTGTC
CGGTGCCCTG AATGAACTGC AAGACGAGGC AGCGCGGCTA TCGTGGCTGG
CCACGACGGG CGTTCCTTGC GCAGCTGTGC TCGACGTTGT CACTGAAGCG
GGAAGGGACT GGCTGCTATT GGGCGAAGTG CCGGGGCAGG ATCTCCTGTC
ATCTCACCTT GCTCCTGCCG AGAAAGTATC CATCATGGCT GATGCAATGC
GGCGGCTGCA TACGCTTGAT CCGGCTACCT GCCCATTCGA CCACCAAGCG
AAACATCGCA TCGAGCGAGC ACGTACTCGG ATGGAAGCCG TCTTGTCGA
TCAGGATGAT CTGGACGAAG AGCATCAGGG GCTCGCGCCA GCCGAACTGT
TCGCCAGGCT CAAGGCGAGC ATGCCCGACG GCGAGGATCT CGTCGTGACC
CATGGCGATG CCTGCTTGCC GAATATCATG GTGGAAAATG GCCGCTTTTC
TGGATTCATC GACTGTGGCC GGCTGGGTGT GGCGGACCGC TATCAGGACA
TAGCGTTGGC TACCCGTGAT ATTGCTGAAG AGCTTGGCGG CGAATGGGCT
(cont. in Fig. 3C)

FIGURE 3B (cont. from Fig. 3B)
```
GACCGCTTCC TCGTGCTTTA CGGTATCGCC GCTCCCGATT CGCAGCGCAT
CGCCTTCTAT CGCCTTCTTG ACGAGTTCTT CTGAGCGGGA CTCTGGGGTT
CGAAATGACC GACCAAGCGA CGCCCAACCT GCCATCACGA GATTTCGATT
CCACCGCCGC CTTCTATGAA AGGTTGGGCT TCGGAATCGT TTTCCGGGAC
GCCGGCTGGA TGATCCTCCA GCGCGGGGAT CTCATGCTGG AGTTCTTCGC
CCACCCTAGG GGGAGGCTAA CTGAAACACG GAAGGAGACA ATACCGGAAG
GAACCCGCGC TATGACGGCA ATAAAAAGAC AGAATAAAAC GCACGGTGTT
GGGTCGTTTG TTCATAAACG CGGGGTTCGG TCCCAGGGCT GGCACTCTGT
CGATACCCCA CCGAGACCCC ATTGGGGCCA ATACGCCCGC GTTTCTTCCT
TTTCCCCACC CCACCCCCCA AGTTCGGGTG AAGGCCCAGG GCTCGCAGCC
AACGTCGGGG CGGCAGGCCC TGCCATAGCC TCAGGTTACT CATATATACT
TTAGATTGAT TTAAAACTTC ATTTTTAATT TAAAAGGATC TAGGTGAAGA
TCCTTTTTGA TAATCTCATG ACCAAAATCC CTTAACGTGA GTTTTCGTTC
CACTGAGCGT CAGACCCCGT AGAAAAGATC AAAGGATCTT CTTGAGATCC
TTTTTTTCTG CGCGTAATCT GCTGCTTGCA AACAAAAAAA CCACCGCTAC
CAGCGGTGGT TTGTTTGCCG GATCAAGAGC TACCAACTCT TTTTCCGAAG
GTAACTGGCT TCAGCAGAGC GCAGATACCA AATACTGTCC TTCTAGTGTA
GCCGTAGTTA GGCCACCACT TCAAGAACTC TGTAGCACCG CCTACATACC
TCGCTCTGCT AATCCTGTTA CCAGTGGCTG CTGCCAGTGG CGATAAGTCG
TGTCTTACCG GGTTGGACTC AAGACGATAG TTACCGGATA AGGCGCAGCG
GTCGGGCTGA ACGGGGGGTT CGTGCACACA GCCCAGCTTG GAGCGAACGA
CCTACACCGA ACTGAGATAC CTACAGCGTG AGCTATGAGA AAGCGCCACG
CTTCCCGAAG GGAGAAAGGC GGACAGGTAT CCGGTAAGCG GCAGGGTCGG
AACAGGAGAG CGCACGAGGG AGCTTCCAGG GGGAAACGCC TGGTATCTTT
ATAGTCCTGT CGGGTTTCGC CACCTCTGAC TTGAGCGTCG ATTTTTGTGA
TGCTCGTCAG GGGGGCGGAG CCTATGGAAA AACGCCAGCA ACGCGGCCTT
TTTACGGTTC CTGGCCTTTT GCTGGCCTTT TGCTCACATG TTCTTTCCTG
CGTTATCCCC TGATTCTGTG GATAACCGTA TTACCGCCAT GCAT
```

FIGURE 3C

USE OF THE CATHELICIDIN LL-37 AND DERIVATIVES THEREOF FOR WOUND HEALING

CROSS-REFERENCE

This application is a divisional of application Ser. No. 13/193,131 filed on Jul. 28, 2011, which claims the benefit to application Ser. No. 12/232,215 filed on Sep. 12, 2008, now U.S. Pat. No. 8,012,933 B2, which issued on Sep. 6, 2011. application Ser. No. 12/232,215 is a divisional of application Ser. No. 10/543,659 filed on Jul. 28, 2005, now U.S. Pat. No. 7,452,864, which issued on Nov. 18, 2008. application Ser. No. 10/543,659 is the national stage of PCT International Application No. PCT/SE2004/000111 filed Jan. 28, 2004, which claims the benefit of priority of Application No. SE 0300207-8 filed in Sweden on Jan. 29, 2003 and U.S. Application No. 60/444,964 filed on Feb. 5, 2003. The entire contents of each of these applications are hereby incorporated by reference.

TECHNICAL FIELD

The present invention refers to the peptide LL-37 and N-terminal fragments, as well as functional derivatives thereof, which peptides can be used for cell proliferation, epithelial repair, and wound healing, and to a pharmaceutical composition comprising one or more of said peptides.

BACKGROUND OF THE INVENTION

Epithelia constitute the primary barrier between host and the potentially harmful environment, and therefore the protection of this interface is vital. A wound represents a broken barrier and immediately sets in motion a series of tightly orchestrated events with the purpose to promptly reinstate the integrity of the barrier. Urgent wound closure has evolved in higher organisms, diverging from the time-consuming process of complete regeneration of tissue seen in lower species. Impaired wound healing represents a major challenge in clinical medicine ranging from the relative delay in "normal" healing seen with increasing age to pathologic non-healing ulcers.

Chronic ulcers constitute a major clinical problem and although our understanding of the physiologic wound process has increased over the past decades only minor Chronic ulcers constitute a major clinical problem and although our understanding of the physiologic wound process has increased over the past decades only minor therapeutic improvements have been attained. Distinct etiologies may underlie the development of ulcerations in different clinical conditions but, whatever the cause, non-healing ulcers are characterized by an inability of the epithelium to migrate, proliferate and close the barrier defect. The most common type of chronic skin ulcers is leg ulcers due to venous insufficiency. These patients develop peripheral venous oedema with subsequent ulceration of the skin, whereas the arterial circulation is intact. Leg and foot ulcers due to arteriosclerotic deficiencies are less common.

In addition, skin ulcers develop in association with immune diseases such as pyoderma gangrenosum and vasculitis. Current treatment includes long-term systemic immunosuppression and is not always effective. Epithelial defects and ulcers in the oral, genital and gastrointestinal mucous membranes are common and cause much distress. The underlying pathomechanisms are not always clear, such as in aphtae and erosive lichen and treatment is poor.

Traditional wound care involves removal, mechanically or enzymatically, of necrotic debris to allow formation of granulation tissue. Wounds that are heavily colonized with bacteria may require antiseptic treatment to prevent invasive infection. Numerous topical anti-microbial agents are used, such as iodine, chlorhexidine, hydrogen peroxide, silver and antibiotics, but the risk of toxic effects of these agents on the matrix and the neoepidermis must be considered. Once the wound is clean of necrotic tissue, dressings should be used to promote granulation tissue formation. A large variety of such dressings are available and numerous animal studies and clinical trials have demonstrated their beneficial effect on wound healing.

A certain proportion of wounds remain therapy-resistant and there is need for additional treatment. During the past decade there has been much focus on the potential use of growth factors to accelerate wound repair. Growth factors are molecules, which control cellular processes that are critical in tissue repair, including cell migration, proliferation, angiogenesis and de novo synthesis of extracellular matrix. The beneficial effect of such growth factors has been suggested in a wide variety of trials (Scharffetter-Kochanek et al., *Basic Res Cardiol* 93:1-3, 1999). However, to date growth factor treatment of chronic ulcers has been largely disappointing in clinical practice. At present becaplermin (Regranex®), licensed in U.S. and Europe but not in Sweden, is the only growth factor for use, preferentially in diabetic foot ulcers. The reasons for clinical failure of growth factors in the treatment of chronic ulcers are thought to involve delivery problems and rapid degradation.

In parallel, there has been development of tissue therapies using auto-logous and allogenic materials in bioengineered human skin equivalents. Cultured epidermal keratinocytes constitute a functioning treatment for coverage of large areas of injured skin in e.g. burn patients, but is expensive, time consuming and requires laboratory facilities. To provide a dermal substrate multiple strategies have been used such as acellular human cadaver and bovine collagen with or without cells. All methods available have considerable disadvantages such as potential transmission of disease and high costs and are hardly suited for basic wound care.

Antimicrobial peptides are effector molecules of the innate immune system, which serve to protect the host against potentially harmful microorganisms. They are conserved through evolution and are widespread in nature. In human, only a handful has been identified so far; among which the defensins and the human cathelicidin antimicrobial peptide hCAP 18 have been implicated in epithelial defense (Selsted et al., *J Biol Chem* 258:14485-14489, 1983).

WO 96/08508 relates to the human polypeptide FALL-39, as well as to pharmaceutical compositions containing said peptide and having an antimicrobial activity against bacteria. The peptide was named FALL-39 after the first four amino acid residues and consisted of the 39 amino acid C-terminal part of a proprotein concomitantly identified by three separate groups (Cowland et al., *FEBS*, 1995; Agerberth et al., *Proc Natl Acad Sci USA* 1995; Larrick et al., *FEBS Letters* 1996). The peptide was shown to have potent antimicrobial activity against both gram-positive and gram-negative bacteria. Further characterization of the C-terminal peptide demonstrated a shorter sequence comprising 37 amino acids excluding the first two (FA) resulting in LL-37, which is the accepted current designation (Gudmundsson et al., *Eur J Biochem* 238: 325-332, 1996).

The proprotein was named hCAP18, human cationic antimicrobial protein, and is a member of the cathelicidin family of proteins consisting of cathelin, which has been conserved through evolution and a C-terminal part, variable in different species. In man, hCAP 18 is the only member of this protein family, whereas in other species, such as mouse and pig, there are several members. The C-terminal peptide LL-37 is thought to function extracellularly and there is no evidence for intracellular cleavage of the proprotein. hCAP18/LL-37 is present in leukocytes and in barrier organs such as skin, mucous membranes, respiratory epithelium and reproductive organs. The localization of hCAP18/LL-37 to barrier epithelia seems to be consistent with a protective role for the peptide in preventing local infection and systemic microbial invasion. LL-37 is described as a cysteine-free peptide that can adopt an amphiphatic, or in other words amphiphilic, α-helical conformation. A high cationicity in combination with a stabilized amphiphatic α-helical structure seems to be required for the anti-microbial effect of such peptides against gram-positive bacteria and fungi, as has been shown experimentally (Gianga-spero et al., *Eur J Biochem* 268:5589-5600, 2001). The amphiphatic and α-helical structure seems to be less critical for killing of gram-negative bacteria. In association with inflammation hCAP18/LL-37 is upregulated in skin epithelium (Frohm et al., *J Biol Chem* 272:15258-15263, 1997) and mucous membranes (Frohm Nilsson et al., *Infect Immun* 67:2561-2566, 1999).

PRIOR ART

Dorschner et al., *J Invest Dermatol* 117:91-97, 2001, demonstrated that the expression of cathelicidins was increased in human and murine skin after incision, and that lack of the murine homologue cathelicidin gene fails to protect against invasion of Group A streptococci in such mice.

WO 96/09322, Children's Medical Center Corporation, discloses that the antibacterial peptide PR-39 possesses syndecan-1 and -4 inductive activity and therefore simultaneously could reduce infection and, as a synducin, influence the action of growth factors, matrix components, and other cellular effectors involved in tissue repair. The synducins could be administered in a pharmaceutical carrier, such as conventional liposomes.

EP 0 935 965 A1, Toray Industries, Inc., refers to an anti-pylori agent containing an anti-microbial peptide, such as the porcine peptide PR-39, as an active agent. It is concluded that exogeneous administration of PR-39 has anti-microbial activity against *Helicobacter pylori* and accelerates healing of gastric ulcers in rat. FALL39 is mentioned as one of the members of the cathelin family.

U.S. Pat. No. 6,255,282, Helix Biomedix, Inc., discloses novel synthetic lytic peptides sharing structural and functional properties of different known lytic peptides. Especially a peptide of 18 to about 40 amino acids and having an α-helical conformation is described. The lytic cathelicidin peptides, however, are not mentioned.

Frohm Nilsson, *Thesis*, Karolinska Institutet, Stockholm 2001, concomit-antly demonstrated that human cathelicidin anti-microbial protein, hCAP 18, is induced in human skin wounding, with high levels and release of active C-terminal peptide, LL-37, in physiological healing but not in chronic non-healing ulcers. hCAP18 was detected in the wound bed and in the epithelium during normal wound healing but was absent in the epithelium of chronic leg ulcers and was detected only in the wound bed and stroma. It was speculated that low levels of hCAP18 and the lack thereof in the epithelium of chronic ulcers contribute to impaired healing.

Zasloff, *Nature* 415:389-395, 2002, in a review of anti-microbial peptides discusses the diverse applications, which have been demonstrated for said peptides as anti-infective agents, and anti-microbial peptides in pharmaceutical development are described.

EP 1 358 888 A1, Bals et al., having a date of publication of Nov. 5, 2003, relates to the use of the peptide LL-37 for prevention or treatment of a disease caused by reduced blood flow and arteriosclerosis and for treatment of wounds due to reduced arterial blood supply. The ability of LL-37 to induce formation of new blood vessels and to stimulate proliferation of endothelial cells is shown. The invention relates entirely to the angiogenetic effect and there is no mentioning of epithelia.

Although a therapeutic use of anti-microbial peptides, in particular LL-37, has been suggested, this has so far not been realized. At high concentrations of the peptide, LL-37 exerts a cytotoxic effect. The potential cytotoxic effects exerted by LL-37 are, however, inhibited in the presence of serum, but pharmaceutical formulations containing serum should be avoided due to risk for transmitting diseases, restricted accessibility and high costs.

SUMMARY OF THE INVENTION

The human anti-microbial peptide hCAP 18 is up-regulated in skin epithelium as a normal response to injury. However, in chronic non-healing leg ulcers only low levels of hCAP18 were found. Notably, in the chronic leg ulcers, hCAP18 and LL-37 were entirely absent in the epithelium but present in the inflammatory infiltrate in the wound bed and in the stroma. We have now shown that hCAP18 is induced during re-epithelialization of organ-cultured skin wounds, and that this re-epithelialization was inhibited by antibodies against LL-37 in a concentration-dependant manner. These findings suggest that LL-37 plays a crucial role in wound closure, functioning as a growth factor. The invention concerns the use of LL-37 or a new synthetic peptide derived from LL-37 or a functional derivative thereof, to compensate for the lack of natural LL-37 produced in vivo.

It was also shown that up-regulation of hCAP18 and/or adding LL-37 peptide stimulate proliferation of normal epithelial and stromal cells, suggesting that normal wound healing and epithelial regeneration could also be enhanced.

It was also found that the cytotoxicity of LL-37 could be reduced in a composition comprising certain lipids.

BRIEF DESCRIPTION OF THE DRAWINGS

FIGS. 3A, 3B, and 3C show the cDNA sequence (SEQ ID NO: 21) of the pIRES2-EGFP vector including the coding sequence for hCAP18, used for transgenic expression of hCAP 18.

DESCRIPTION OF THE INVENTION

Figure 1:
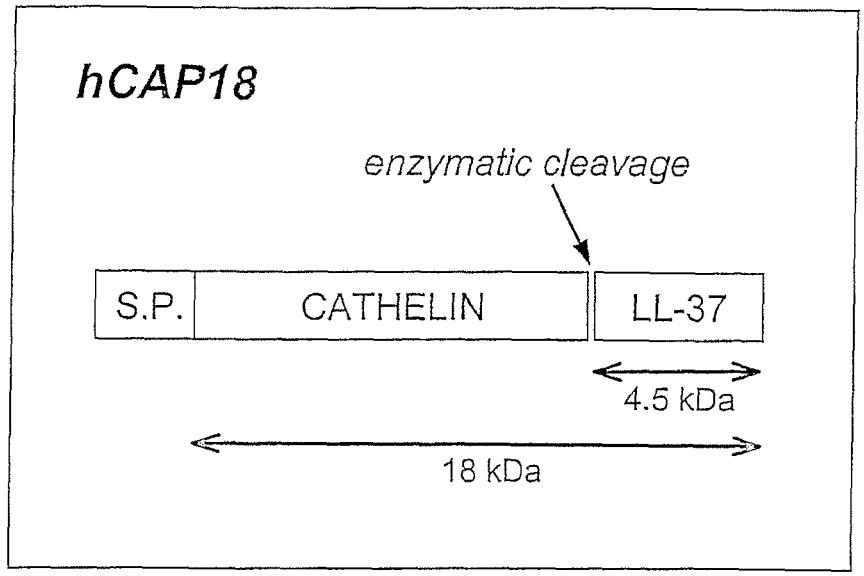
FIG. 1 is a schematic drawing of the 18 kDa hCAP18 protein consisting of a signal peptide, S.P., the conserved cathelin part, and the anti-microbial peptide LL-37, which is enzymatically cut off in vivo.

The present invention refers to a peptide having a sequence of at least 20 amino acids of the N-terminal fragment of LL-37, with the proviso that LL-37 is excluded, as well as to pharmaceutically acceptable salts and derivatives thereof. LL-37 has the amino acid sequence SEQ ID NO 1:

H-Leu-Leu-Gly-Asp-Phe-Phe-Arg-Lys-Ser-Lys-Glu-Lys-
Ile-Gly-Lys-Glu-Phe-Lys-Arg-Ile-Val-Gln-Arg-Ile-
Lys-Asp-Phe-Leu-Arg-Asn-Leu-Val-Pro-Arg-Thr-Glu-
Ser-OH.

The N-terminal sequence of LL-37 refers to a sequence beginning with the amino acid residue number 1 of leucine, Leu.

Pharmaceutically acceptable salts contain for instance the counterions acetate, carbonate, phosphate, sulphate, trifluoroacetate, and chloride. A preferred salt is the acetate. Esters and amides are examples of pharmaceutically acceptable derivatives.

The peptide of the invention should have an amino acid chain of no more that 40 amino acids. The invention refers to a peptide having the sequence of LL-37 to which 1-3 amino acids have been added in the C-terminal end. Any amino acid selected from Ala, Arg, Asn, Asp, Cys, Gln, Glu, Gly, His, Ile, Leu, Lys, Met, Phe, Pro, Ser, Thr, Trp, Tyr, Val, as well as derivatives thereof can be added. An example of a peptide having 38 amino acids, LL-38, SEQ ID NO 19, has the sequence of LL-37 to which serine has been added in the C-terminal end.

The invention especially refers to a peptide having a sequence of at least 20 amino acids and selected from the group consisting of LL-36, LL-35, LL-34, LL-33, LL-32, LL-31, LL-30, LL-29, LL-28, LL-27, LL-26, LL-25, LL-24, LL-23, LL-22, LL-21 and LL-20, having the sequence SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, and SEQ ID NO 18, respectively.

Preferred peptides are selected from the groups consisting of LL-36, LL-35, LL-34, LL-33, LL-32, LL-31, LL-30, LL-29, LL-28, LL-27, LL-26, and LL-25.

The amino acid sequences of the peptides of the invention are given in the following table.

| SEQ ID NO | Peptide | Amino Acid Sequence |
|---|---|---|
| 1 | LL-37 | LLGDFFRKSKEKIGKEFKRIVQRIKDFLRNLVPRTES |
| 2 | LL-36 | LLGDFFRKSKEKIGKEFKRIVQRIKDFLRNLVPRTE |
| 3 | LL-35 | LLGDFFRKSKEKIGKEFKRIVQRIKDFLRNLVPRT |
| 4 | LL-34 | LLGDFFRKSKEKIGKEFKRIVQRIKDFLRNLVPR |
| 5 | LL-33 | LLGDFFRKSKEKIGKEFKRIVQRIKDFLRNLVP |
| 6 | LL-32 | LLGDFFRKSKEKIGKEFKRIVQRIKDFLRNLV |
| 7 | LL-31 | LLGDFFRKSKEKIGKEFKRIVQRIKDFLRNL |
| 8 | LL-30 | LLGDFFRKSKEKIGKEFKRIVQRIKDFLRN |
| 9 | LL-29 | LLGDFFRKSKEKIGKEFKRIVQRIKDFLR |
| 10 | LL-28 | LLGDFFRKSKEKIGKEFKRIVQRIKDFL |
| 11 | LL-27 | LLGDFFRKSKEKIGKEFKRIVQRIKDF |
| 12 | LL-26 | LLGDFFRKSKEKIGKEFKRIVQRIKD |
| 13 | LL-25 | LLGDFFRKSKEKIGKEFKRIVQRIK |
| 14 | LL-24 | LLGDFFRKSKEKIGKEFKRIVQRI |
| 15 | LL-23 | LLGDFFRKSKEKIGKEFKRIVQR |
| 16 | LL-22 | LLGDFFRKSKEKIGKEFKRIVQ |
| 17 | LL-21 | LLGDFFRKSKEKIGKEFKRIV |
| 18 | LL-20 | LLGDFFRKSKEKIGKEFKRI |
| 19 | LL-38 | LLGDFFRKSKEKIGKEFKRIVQRIKDFLRNLVPRTESS |

The new peptides can be used as a medicament for cell proliferation, epithelial regeneration, healing of normal or chronic wounds, and as antimicrobial agents.

The new peptides are believed to have the potential to form an α-helical structure at physiological conditions.

According to another aspect the invention refers to the use of a peptide having an amino acid sequence selected from the group consisting of
a) SEQ ID NO 1;
b) a sequence containing at least 20 amino acids of the N-terminal fragment of SEQ ID NO 1;
and pharmaceutically acceptable salts or derivatives thereof, which peptide enhances proliferation of epithelial and/or stromal cells through a non-lytic mechanism, for the preparation of a medicament for epithelial regeneration, and healing of wound epithelium and stroma.

The present invention especially refers to the use of the peptide LL-37 having the amino acid sequence SEQ ID NO 1, in the form of a salt, preferably an acetate salt.

The invention also refers to the use of a peptide, selected from the group consisting of LL-20 to LL-36, as stated above.

LL-37, as well as LL-25 to LL-36, possesses a net positive charge (+5-+7) at neutral pH due to the cationic amino acid residues of lysine and arginine in the primary structure. Especially LL-34 and LL-35 have net positive charge of 7. The other amino acid residues are nonpolar/hydrophobic or polar and neutral, or, to a less extent, polar and negatively charged, which makes the whole peptide molecule amphipatic. Peptides of this type interact electrostatically with the negatively charged phospholipid microbial cell walls inserting the hydrophobic face into the bilayer. A reduction of either hydrophobicity and/or charge reduces the anti-microbial effect of the peptides. The cytotoxic effect exerted by the peptides against host cells, often assessed as hemolytic activity, is shown to correlate with their anti-microbial effects (Chen et al., *FEBS Lett* 236:462-466, 1988). Various studies have confirmed that this is true also for other amphipatic α-helical anti-microbial peptides.

Studies of the C-terminal peptide, having a length of 37 amino acids, of rabbit CAP 18 (Cap18$_{106\text{-}142}$) show that broad-spectrum antibacterial activity is retained in the highly basic 20 residue N-terminal sequence, but not if the N-terminus is truncated (Larrick et al., *Antimicrob Agents Chemother* 37:2534-2539, 1993).

LL-37, as well as the new peptides LL-20 to LL-36, can be synthesized using an automatic peptide synthesizer and standard methods for peptide syntheses.

The invention especially refers to the use of the LL-37 peptide or anyone of the peptides LL-20 to LL-36 for the preparation of a medicament for treatment of chronic ulcers. Said chronic ulcers can be due to venous insufficiency, such as leg ulcers, metabolic dysfunction, such as diabetes, or immunological diseases, such as vasculites, and pyoderma gangrenosum. The peptides of the invention can also be used for treatment of wounds due to trauma or burns. The described peptides can especially be used for regeneration of epithelial tissue, and to enhance epidermal regeneration following microdermabrasion.

In addition to being toxic to the cell, LL-37 is rapidly degraded in the wound environment. Serine proteinase 3 was recently shown to be responsible for extracellular cleavage of hCAP18 (Sørensen et al., *Blood* 97:3951-3959, 2001).

In order to prevent decomposition of the peptide and also for reducing the intrinsic cytotoxicity, the peptide can be formulated with a polar lipid carrier. Said formulation should facilitate the administration of the peptide to the wound and will in addition provide a sustained release of the peptide after administration. The stability of the peptide will be improved both in vivo and in vitro.

Another object of the invention is thus a pharmaceutical composition comprising an anti-microbial cathelicidin peptide in the form of pharmaceutically acceptable salts or derivatives thereof in combination with a carrier consisting of a bilayer-forming polar lipid and an aqueous solution.

Figure 2:
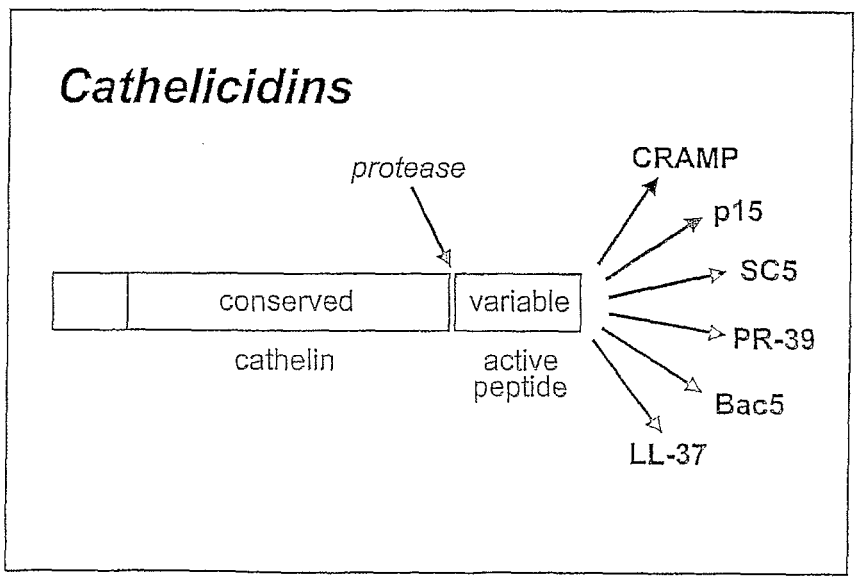
FIG. 2 is a schematic drawing of the cathelicidin protein family, illustrating the diversity of C-terminal peptides in different species.

The cathelicidin peptide can, in addition to LL-37 in human, be derived from different animal species, and is for example SC5 from sheep, Bac5 from cow, PR-39 from pig, CRAMP from mouse, and p15 from rabbit, see FIG. 2.

A bilayer normally refers to the lamellar arrangements of polar lipids in water. The acyl chains form the internal hydrophobic part and the polar head-groups the hydrophilic part of the bilayer. As examples of such polar bilayer-forming lipids, either of natural or synthetic origin, can be mentioned phosphatidylcholine, phosphatidylglycerol, digalactosyldiacylglycerol, sphingomyelin and the like. Depending on the concentration of said polar lipids in polar solvents, such as water, liposomes or viscous gels of the lamellar liquid crystalline type may be formed.

The pharmaceutical composition especially comprises a peptide having an amino acid sequence selected from the group consisting of
  a) SEQ ID NO 1;
  b) a sequence containing at least 20 amino acids of the N-terminal fragment of SEQ ID NO 1;
in the form of pharmaceutically acceptable salts or derivatives thereof in combination with a carrier consisting of a bilayer-forming polar lipid and an aqueous solution.

Preferred bilayer-forming polar lipids to be mixed or formulated with the peptide are those, which are neutral in charge. Especially useful are the digalactosyldiacylglycerols, and other glycolipids, such as the glycosyl ceramides, either natural or synthetic, in which a non-ionic carbohydrate moiety constitutes the polar head-group. Less preferred, but still useful, are those polar lipids, which are zwitterionic and neutral at physiological conditions, such as phosphatidylcholine, phosphatidylethanolamine, and sphingomyelin. Least preferred are those polar lipids, which are negatively charged and thus form strong complexes with the positively charged peptide.

According to the invention said bilayer-forming polar lipid carrier is preferably selected from the group consisting of phospholipids, galactolipids and sphingolipids.

An especially preferred bilayer-forming polar lipid is digalactosyldiacylglycerol or polar lipid mixtures rich in digalactosyldiacylglycerols due to the extremely good cutaneous tolerability of this class of polar lipids. Digalactosyldiacylglycerol is a class of lipids belonging to the glycolipid family, well known constituents of plant cell membranes. One of the most abundant classes contains two galactose units, and the commonly used nomenclature and abbreviation of this is digalactosyldiacylglycerol, DGDG, sometimes referred to as galactolipids. Galactolipids, primarily DGDG and DGDG-rich materials have been investigated and found to be surface active material of interest in industrial applications such as food, cosmetics, and pharmaceutical products. WO 95/20944 describes the use of DGDG-rich material, a "galactolipid material", as a bilayer-forming material in polar solvents for pharmaceutical, nutritional and cosmetic use. Said application does not disclose the use of galactolipids in combination with peptides and proteins in general, particularly not a peptide of the present invention.

According to a preferred aspect the invention refers to a pharmaceutical composition wherein the bilayer-forming polar lipid carrier is a polar lipid mixture rich in digalactosyldiacylglycerols.

Another preferred aspect of the invention is a pharmaceutical composition wherein the peptide is in the form of acetate. A preferred peptide is LL-37 in the form of an acetate salt. Especially preferred is a pharmaceutical composition comprising a combination of an acetate of LL-37 and CPL-Galactolipid as the bilayer-forming lipid carrier. CPL-Galactolipid is a trademark for a galactolipid fraction consisting of 50-70% by weight of digalactosyldiacylglycerols and 30-50% or other polar lipids.

The ratio between the peptide in the form of a salt and a galactolipid carrier in the pharmaceutical composition should preferably be 1:5 to 1:50, especially 1:10-1:25 by weight.

In addition to the bilayer-forming lipid the carrier also contains an aqueous solution. An aqueous solution refers to a solution having physiologically or pharmaceutically acceptable properties regarding pH, ionic strength, isotonicity etc. As examples can be mentioned isotonic solutions of water and other biocompatible solvents, aqueous solutions, such as saline and glucose solutions, and hydrogel-forming materials. The aqueous solution can be buffered, such as phosphate-buffered saline, PBS.

The pharmaceutical composition can in addition comprise pharmaceutically acceptable excipients, such as a preservative to prevent microbial growth in the composition, antioxidants, isotonicity agents, colouring agents and the like. In aqueous suspensions the compositions can be combined with suspending and stabilising agents.

The colloidal nature of the composition makes it possible to prepare the composition aseptically by using a final sterile filtration step.

In order to form a gel the peptide can be preferably formulated with a hydrogel-forming material. Examples of hydrogel-forming materials are synthetic polymers, such as polyvinylalcohol, polyvinylpyrolidone, polyacrylic acid, polyethylene glycol, poloxamer block copolymers and the like; semi-synthetic polymers, such as cellulose ethers, including carboxymethylcellulose, hydroxyethylcellulose, hydroxy-propylcellulose, methylcellulose, methylhydroxypropylcellulose and ethylhydroxy-ethylcellulose, and the like; natural gums, such as acacia, carragenan, chitosan, pectin, starch, xanthan gum and the like.

It is advantageous to use a hydrogel which is muco-adhesive. In that respect it is particularly useful to use hyaluronic acid and derivatives thereof, cross-linked polyacrylic acids of the carbomer and polycarbophil types, polymers that readily form gels, which are known to adhere strongly to mucous membranes.

It is also advantageous to use block copolymers of the poloxamer type, i.e. polymers consisting of polyethylene glycol and polypropylene glycol blocks. Certain poloxamers dispersed in water are thermoreversible: at room temperature they are low viscous but exhibit a marked viscosity increase at elevated temperatures, resulting in a gel formation at body temperature. Thereby the contact time of a pharmaceutical formulation administered to the relatively warm wound may be prolonged and thus the efficacy of the incorporated peptide may be improved.

The pharmaceutical composition of the invention can be formulated for topical or enteral, that is oral, buccal, sublingual, mucosal, nasal, bronchial, rectal, and vaginal administration.

Non-limiting examples of pharmaceutical compositions for topical administration are solutions, sprays, suspensions, emulsions, gels, and membranes. If desired, a bandage or a band aid or plaster can be used, to which the pharmaceutical composition has been added. Tablets, capsules, solutions or suspensions can be used for enteral administration.

According to another aspect the invention refers to the use of a peptide having an amino acid sequence selected from the group consisting of a) SEQ ID NO 1;
b) a sequence containing at least 20 amino acids of the N-terminal fragment of SEQ ID NO 1;

in the form of pharmaceutically acceptable salts or derivatives thereof for proliferation of epithelial and/or stromal cells in vitro through a non-lytic mechanism.

Said proliferation can especially be used for proliferation of human autologous epithelial and stromal cells in vitro.

The invention also refers to a growth medium for culturing eukaryotic cells, such as epithelial and/or stromal cells, which comprises LL-37 or a peptide as described in combination with a basal medium. A cytotoxicity reducing agent can be added, such as serum. Apolipoprotein A-I (apoA-I) has been found to be the main LL-37 binding protein in human plasma and works as a scavenger of LL-37 (Wang et al, *J Biol Chem* 273:33115-33118, 1998; Sørensen et al, *J Biol Chem* 274: 22445-22451, 1999), suggesting a mechanism involved in the regulation of a cathelicidin peptide. The cytotoxicity reducing agent can also be a bilayer-forming polar lipid, such as a lipid selected from the group consisting of phospholipids, galactolipids and sphingolipids, as described above.

The basal medium of the growth medium of the invention is based on double-distilled water, and a number of the following ingredients: inorganic salts, phenol red, glucose, thymidine, hypoxanthinine, HEPES, sodium pyruvate, aminopterin, amino acids and vitamins. For culturing of epithelial cells, such as e.g. keratinocytes, in vitro the growth medium can consist of basal medium and a growth promoting kit including a) LL-37 peptide in a salt solution, b) penicillin+ streptomycin, c) insulin, d) transferrin, e) triiodotyronine, f) hydrocortisone, g) choleratoxin, and a selected cytotoxicity reducing agent, such as serum or a polar lipid. For culturing of stromal cells, such as e.g. fibro-blasts, in vitro, a growth medium can consist of basal medium and a growth promoting kit including a) LL-37 peptide in a salt solution, b) penicillin+ streptomycin, and a selected cytotoxicity reducing agent, such as serum or a polar lipid.

Another object of the invention is a method of enhancing the expansion of human autologous epithelial and stromal cells in vitro for cell transplantation in vivo, wherein cells are isolated from an excised piece of healthy skin, said isolated cells are cultivated in vitro in a growth medium according to the invention, and the cultivated cells are subsequently harvested and used for treatment of wounds, such as burn injuries and ulcers.

The invention also refers to a growth promoting kit comprising the LL-37 peptide or a peptide as described, and a cytotoxicity reducing bilayer-forming polar lipid, optionally in combination with antibiotics, basal media, and other conventional additives in separate containers.

According to still another aspect the invention refers to transfection of a full-length hCAP 18 cDNA construct into autologous human keratinocytes for cell transplantation of ulcers and burns. The cDNA construct is designed to allow regulation of hCAP18 gene expression by a switch mechanism (Resnitzky et al., *Mol Cell Biol* 14:1669-1679, 1994). Autologous human keratinocytes are obtained from a healthy skin piece excised from the patient. The keratinocytes are isolated and expanded in cell culture as described. The cDNA construct is transfected into keratinocytes. The transfected keratinocytes are further expanded in vitro and given back to the patient.

The invention especially refers to the use of a gene construct comprising the complete cDNA sequence of hCAP 18 having the sequence SEQ ID NO 20 for transfection of epithelial and/or stromal cells in order to enhance proliferation of said cells.

EXAMPLES

Example 1

Preparation of Synthetic Peptides

The LL-37 peptide was synthesized according to solid phase synthesis with the 9-fluorenylmethoxycarbonyl/tert-butyl strategy. The crude peptide, as the trifluoroacetate salt, was purified with HPLC and finally isolated by lyophilization (lot 971/26, from PolyPeptide Laboratories A/S, Hilleröd, Denmark). The purity was determined by means of HPLC and area integration and was found to be 99%. The molecular weight was analyzed using mass spectrometry and corresponded to the theoretical value of 4493 g/mol as the free base. Analysis of composition of amino acids showed that the relative amounts of each amino acid corresponded with the theoretical values for LL-37. The peptide content was calculated from the results from the amino acid analysis and found to be 73%, the remainder being counterions and residual solvent.

Several batches of LL-37 were synthesized, and the LL-37 peptide used in the following Examples 2 and 5 was in the form of the acetate salt.

The peptides LL-36 and LL-38 were synthesized correspondingly, in the form of acetate.

The different peptides used in the following examples and tests were as follows.

| Peptide | Counterion | Lot | Purity area-% | Peptide content % (w/w) | Used in | Manufact. Year |
|---|---|---|---|---|---|---|
| LL-37 | Trifluoroacetate | YS 5253 | 98 | | Ex. 3, 4, 6, 7 Test 3 | 1997 |
| LL-37 | Trifluoroacetate | 971/26 | 99 | 73 | Test 5 | 2002 |
| LL-37 | Acetate | 990/37/A | 99 | 83 | Ex. 2, 5 Test 4 | 2003 |

-continued

| Peptide | Counterion | Lot | Purity area-% | Peptide content % (w/w) | Used in | Manufact. Year |
|---|---|---|---|---|---|---|
| LL-38 | Acetate | 990/38 | | | Test 4 | 2003 |
| LL-36 | Acetate | 990/39 | | | Test 4 | 2003 |

Example 2

Preparation of a Pharmaceutical Composition Comprising a Mixture of LL-37 Peptide and Lipid Carrier A pharmaceutical composition was prepared using the following ingredients:

| Ingredient | Concentration |
|---|---|
| LL-37 | 100 ppm* |
| CPL-Galactolipid | 0.20% |
| 2.6% Glycerol in sterile water | ad 100% |

*ppm = parts per million (by weight)

The peptide LL-37, as the acetate salt (lot 990/37/A), and the lipid carrier, CPL-Galactolipid, obtained from Lipocore Holding AB, a lipid material rich in digalactosyl-diacylglycerols and prepared from oats, were weighed in a 50 ml glass flask. The two ingredients were gently mixed and then the glycerol solution was added. The mixture was shaken vigorously for 120 min and then allowed to stand for 1 h. The resulting composition was a fine, homogenous dispersion. It was kept refrigerated until use.

Example 3

Preparation of Aqueous Mixtures Comprising the LL-37 Peptide and a Lipid Carrier Mixtures of LL-37, as the trifluoroacetate salt (lot 971/26) and a polar, bilayer-forming lipid carrier were prepared using the following ingredients (percentages in weight by weight):

TABLE 1

| Ingredient | A1 | A2 | B1 | B2 | C1 | C2 |
|---|---|---|---|---|---|---|
| LL-37 | 100 ppm | — | 90 | — | 92 | — |
| CPL-Galactolipid | 0.19% | 0.20% | — | — | — | — |
| Epikuron 200 | — | — | 0.19% | 0.19% | — | — |
| CPL-Sphingomyelin | — | — | — | — | 0.19% | 0.19% |
| DMEM | ad 100% | ad 100% | ad 100% | ad 100% | ad 100% | ad 100% |

CPL-Galactolipid, obtained from Lipocore Holding AB, is a chromatographically purified galactolipid fraction from oats, Epikuron 200, obtained from Lucas Meyer GmbH, is phosphatidylcholine from soybean, and CPL-Sphingomyelin, obtained from Lipocore Holding AB, is chromatographically purified sphingomyelin from bovine milk. DMEM, Dulbecco's Modified Eagle Medium, from Invitrogen Corp. is an aqueous solution containing inorganic salts, glucose, phenol red, amino acids and vitamins.

The peptide LL-37 and the lipid carrier were weighed in a glass flask and then DMEM was added. The resulting dispersions were vigorously shaken, using a Heidolph Promax mixer at a frequency of 200/min for 1.5 h, and allowed to equilibrate and settle for about 3 h at room temperature. A visual assessment was then made and the following results were obtained: All samples were turbid dispersions and there were no differences in turbidity between any of the samples B1, B2, C1, and C2. The only observed difference was between samples A1 and A2: the former, containing the peptide, was significantly less turbid than the latter, without the peptide. Sample A2 was slightly less turbid than, in turn, samples B1, B2, C1, and C2. These observations indicate a stronger interaction between the two components in sample A1, which results in a smaller average particle size of the dispersion, compared to the peptide-free sample A2, but also compared to the rest of the corresponding samples. After one day of storage at room temperature samples A1 and A2 were unchanged, i.e. both were homogeneous dispersions and A1 less turbid than A2, whereas the four other samples had considerable sediments on the bottom of the glass flasks.

All three mixtures of peptide and polar lipid carrier are useful for various purposes, e.g. as delivery systems and for tests in cell cultures; however, since the shelf-life of the mixtures of peptide and galactolipid is considerably longer (no sediment-ation) than that of the others, said mixtures are the most preferred for practical use.

Example 4

Preparation of Aqueous Mixtures Comprising a Mixture of LL-37 Peptide and Lipid Carrier Samples of LL-37 as trifluoroacetate (lot 971/26) and a polar, bilayer-forming lipid carrier were prepared using the following ingredients (percentages in weight by weight):

TABLE 2

| Ingredient | Sample D | Sample E | Sample F | Sample G | Sample H | Sample I | Sample J |
|---|---|---|---|---|---|---|---|
| LL-37 | 96 ppm | 100 ppm | 100 ppm | 103 ppm | 100 ppm | 100 ppm | 100 ppm |
| CPL-Galactolipid | 0.21% | — | — | — | 0.20% | — | — |
| PC from soybean, 40% | — | 0.21% | — | — | — | — | — |
| PC from egg yolk, 60% | — | — | 0.21% | — | — | — | — |
| DOPC, 99% | — | — | — | 0.20% | — | — | — |
| PC from soybean, 70% | — | — | — | — | — | 0.20% | — |
| PC from soybean, 94% | — | — | — | — | — | — | 0.20% |
| PBS | ad 100% | ad 100% | ad 100% | ad 100% | ad 100% | ad 100% | ad 100% |

CPL-Galactolipid, manufactured by LTP Lipid Technologies Provider AB, is a chromatographically purified galactolipid fraction from oats. The various phospholipids used were phosphatidylcholine (PC) from soybean, approximately 40% (Sigma; P-3644); PC from dried egg yolk, approximately 60% (Sigma; P-5394); synthetic dioleylphosphatidylcholine (DOPC), approximately 99% (Sigma; P-6354); PC from soybean, approximately 70% (Lipoid S75); and PC from soybean, approximately 94% (Lipoid S100). PBS is phosphate-buffered saline from Invitrogen Corp. (Dulbecco's; cat. no. 14190-094).

All the investigated polar lipids have chain melting phase transition temperatures well below 0° C., i.e., in the range of −10 to −15° C., when fully hydrated.

The peptide LL-37 and the lipid carrier were weighed in a 100 ml glass flask and then PBS was added. The total volume was about 30 ml. The samples were vigorously shaken, using an ST mixer (type B1, E. Büchler, Tübingen) set at 5.5 (corresponding to an approximate frequency of 150/min) for 2 h, and allowed to equilibrate and settle for about 30 min at room temperature. The turbidity of the resulting dispersions was then recorded at 400-800 nm on a Shimadzu UV-VIS Spectrophoto-meter UV-160A. The measurements were made against pure water at room tempera-ture using a 10 mm cuvette cell. Turbidity data in Table 3 are presented as % trans-mission at 600 nm. Visual assessments of the dispersions were also made. Turbidity measurements were repeated after one and two days of storage at room temperature of the dispersions.

TABLE 3

Turbidity Data

| Turbidity (λ = 600 nm) | Sample D | Sample E | Sample F | Sample G | Sample H | Sample I | Sample J |
|---|---|---|---|---|---|---|---|
| 30 min | 64.1% | 70.9% | 5.1% | 1.7% | 68.6% | 18.6% | 1.4% |
| 1 day | 57.3% | 65.6% | — | — | 67.0% | 19.8% | — |
| 2 days | 57.2% | 65.5% | — | — | 66.9% | 20.5% | — |

From the visual assessments it was concluded that all mixtures formed more or less turbid dispersions; samples D, E, H, and I formed the least turbid dispersions, manifested in the highest transmission of light in Table 3, whereas samples F, G, and J formed the most turbid dispersions and consequently gave rise to the lowest trans-mission of light detected by the spectrophotometer. After one day of storage at room temperature, samples F, G, and J with the initially high turbidity (low transmission) had all sedimented and were not measured. Samples D, E, H, and I were all stable dispersions and resulted in reproducible turbidity data, after one and two days after preparation.

Samples D and H are duplicates, both containing CPL-Galactolipid but sample H had a slightly higher weight ratio of peptide to galactolipid. This resulted in a slightly lower turbidity (higher transmission) in sample H suggesting that the interaction between peptide and lipid in this sample is stronger than that in sample D, leading to smaller complexes/aggregates which give rise to lower turbidity.

Samples D, E, H, and I were further monitored with respect to colloidal stability at 2-8° C. for 2 months.

TABLE 4

Stability Data

| Sample | Appearance | Stability |
|---|---|---|
| D | fine turbid dispersion, slight sedimentation, easy to redisperse sediment | acceptable |
| E | turbid dispersion, slight sedimentation; microbial growth | not acceptable |
| H | fine turbid dispersion, slight sedimentation, easy to redisperse sediment | acceptable |
| I | turbid dispersion, slight sedimentation; microbial growth | not acceptable |

These data and observations show that two mixtures of peptide and polar lipid carrier are better than the rest of the tested mixtures. The carriers containing CPL-Galactolipid (sample D and H) and PC from soybean, ca 40% (sample E) gave rise to the most finely dispersed systems with the longest colloidal stability; however, it is only CPL-Galactolipid which is acceptable for pharmaceutical use, since the phospholipid material with only 40% phosphatidylcholine may be used for technical applications only. These data again demonstrate the usefulness of the galactolipid material in various pharmaceutical applications, e.g. as a carrier system for peptides.

Example 5

Preparation of Aqueous Mixtures Comprising Varying Contents of LL-37 Peptide and Varying Contents of Galactolipid A stock solution of LL-37 peptide (acetate salt; lot 990/37/A) in PBS, 995 ppm, and a stock solution of CPL-Galactolipid, 1.00%, in PBS were prepared. Aliquots of the stock solutions plus additional PBS were mixed in 20 ml glass vials with rubber stoppers and aluminum caps. The compositions of the mixtures are presented in Table 5. After equilibration at room temperature for 1 h, the vials were shaken in horizontal position on an ST mixer (type B1, E. Büchler, Tübingen), set at 7.5 (corresponding to an approximate frequency of 190/min), for 1 h. The mixtures were then allowed to equilibrate and settle over night at room temperature. The appearances of the mixtures after one and five days a 4° C. were evaluated as: clear colloidal, slightly turbid, turbid, milky, and the results are summarized in Table 5.

TABLE 5

| Sample Number | LL-37 (ppm) | Galacto-lipid (%) | Peptide: Lipid (w/w) | Appearance after 1 Day | Appearance after 5 Days |
|---|---|---|---|---|---|
| 01 | 247 | 0.135 | 1:5.5 | turbid dispersion, sediment | turbid dispersion, sediment |
| 02 | 181 | 0.133 | 1:7.4 | clear colloidal solution | clear colloidal solution, slight sediment |
| 03 | 116 | 0.133 | 1:11 | clear colloidal solution | clear colloidal solution |
| 04 | 50.5 | 0.135 | 1:27 | clear colloidal solution | clear colloidal solution |
| 05 | 16.5 | 0.133 | 1:81 | slightly turbid dispersion, homogeneous | slightly turbid dispersion, homogeneous |
| 06 | 8.2 | 0.135 | 1:165 | turbid dispersion, homogeneous | turbid dispersion, homogeneous |
| 07 | — | 0.133 | — | turbid dispersion, homogeneous | turbid dispersion, homogeneous |

TABLE 5-continued

| Sample Number | LL-37 (ppm) | Galacto-lipid (%) | Peptide: Lipid (w/w) | Appearance after 1 Day | Appearance after 5 Days |
|---|---|---|---|---|---|
| 08 | 248 | 0.266 | 1:11 | clear colloidal solution | clear colloidal solution, slight sediment |
| 09 | 182 | 0.267 | 1:15 | clear colloidal solution | clear colloidal solution |
| 10 | 116 | 0.266 | 1:23 | clear colloidal solution | clear colloidal solution |
| 11 | 49.8 | 0.268 | 1:54 | slightly turbid dispersion, homogeneous | slightly turbid dispersion, homogeneous |
| 12 | 17.1 | 0.266 | 1:156 | slightly turbid dispersion, homogeneous | slightly turbid dispersion, homogeneous |
| 13 | 8.9 | 0.265 | 1:298 | slightly turbid dispersion, homogeneous | slightly turbid dispersion, homogeneous |
| 14 | — | 0.265 | — | slightly turbid dispersion, homogeneous | slightly turbid dispersion, homogeneous |
| 15 | 247 | 0.532 | 1:22 | clear colloidal solution | clear colloidal solution |
| 16 | 182 | 0.532 | 1:29 | slightly turbid dispersion, homogeneous | slightly turbid dispersion, homogeneous |
| 17 | 116 | 0.533 | 1:46 | turbid dispersion, homogeneous | turbid dispersion, homogeneous |
| 18 | 49.2 | 0.533 | 1:108 | turbid dispersion, homogeneous | turbid dispersion, homogeneous |
| 19 | 16.5 | 0.534 | 1:324 | turbid dispersion, homogeneous | turbid dispersion, homogeneous |
| 20 | 8.2 | 0.532 | 1:649 | turbid dispersion, homogeneous | turbid dispersion, homogeneous |
| 21 | — | 0.533 | — | turbid dispersion, homogeneous | turbid dispersion, homogeneous |
| 22 | 248 | 0.799 | 1:32 | turbid dispersion, homogeneous | turbid dispersion, slight sediment |
| 23 | 182 | 0.802 | 1:44 | milky dispersion, homogeneous | milky dispersion, slight sediment |
| 24 | 115 | 0.801 | 1:70 | milky dispersion, homogeneous | milky dispersion, slight sediment |
| 25 | 50.1 | 0.799 | 1:159 | milky dispersion, homogeneous | milky dispersion, slight sediment |
| 26 | 16.8 | 0.799 | 1:476 | milky dispersion, homogeneous | milky dispersion, slight sediment |
| 27 | 8.6 | 0.798 | 1:928 | milky dispersion, homogeneous | milky dispersion, slight sediment |
| 28 | — | 0.798 | — | milky dispersion, homogeneous | milky dispersion, slight sediment |

It is clear that certain ratios of LL-37 peptide and galacto-lipid give rise to an appearance in solution, which indicate the presence of small complexes, smaller in size than particles of the corresponding samples without LL-37. A clear solution indicates a superior colloidal stability.

Example 6

Conformational Measurements

Measurements of circular dichroism (CD) of LL-37 in solution may reveal information about conformational changes. The antibacterial activity of LL-37 is dependent on the conformation: a high content of helical content results in a strong antibacterial action and a high cytotoxic activity (Johansson et al., *J Biol Chem* 273:3718-3724, 1998). It has been found that the α-helical conformation of LL-37 is dependent on the counterion, the pH, and the peptide concentration (Johansson et al., *J Biol Chem* 273:3718-3724, 1998). It is also known that a certain fraction of the peptide has an α-helical structure in aqueous solution and that this structure may be promoted by the presence of additives such as lipids, transforming it from a random coil to an α-helix (Turner et al., *Antimicrob Agents Chemother* 42:2206-2214, 1998).

Samples for circular dichroism (CD) measurements were prepared in 10 mM aqueous phosphate buffer solution, pH 7.0, containing 200 ppm LL-37 (as the trifluoroacetate, lot 971/26), with and without 0.40% CPL-Galactolipid. The samples, 20 ml in 50 ml glass flasks, were vigorously shaken with an ST mixer (type B1, E. Büchler, Tübingen) set at 7.5 (corresponding to an approximate frequency of 220/min) for 2 h. They were then allowed to equilibrate and settle over night at 2-8° C.

CD spectra were recorded on a Jasco J-720 (Jasco Inc.) spectropolari-meter. The sample compartment with the cuvette cell (1 mm path length) was placed near the photo-multiplier, in order to reduce effects of light scattering from the disper-sions. The samples were measured at room temperature and scanned from 280 to 200 nm at a rate of 20 nm/min, with a resolution of 1 nm and 3 accumulations per run. The results are expressed as the mean residue ellipticity, $[\theta]$, and the percentage of α-helical conformation at 222 nm is estimated by the following formula: $([\theta]_{222}+3900) \cdot 100/41900$.

The CD measurements on 200 ppm LL-37 in 10 mM phosphate buffer solution, pH 7.0, revealed an α-helical secondary structure by double dichroic minima at 208 and 222 nm. The minimum at 222 nm was used to calculate the percentage α-helical structure, which was found to be about 63%. When the galactolipid was added at a concentration of 0.40% (w/w) in the same buffer solution the α-helical structure of LL-37 was practically unaffected, with an approximate α-helical structure of 64%.

Enhanced helical conformation is related to increased antibacterial activity. It is speculated that the secondary structure is also relevant for the wound healing capacity of LL-37, where a high percentage of α-helical structure means enhanced activity. In an aqueous buffer solution this also means high cytotoxicity, but in the presence of galactolipid the secondary structure is retained, and thus the activity is unaffected, whereas the cytotoxicity is diminished.

An anionic synthetic phospholipid, palmitoyl-oleoyl-phosphatidylglycerol (POPG; Sigma-Aldrich, P6956) was used as a reference and tested using the same experimental conditions as described above. A lower percentage of α-helical structure, 58%, was found when this lipid was present, indicating that the conformation and thus activity of LL-37 is more influenced by the negatively charged phospholipid than by the neutral galactolipid. However, more importantly, after one month of storage at 4° C. the sample had partially separated, with sediments on the bottom of the container. Gentle shaking resulted in a coarse dispersion. At the same timepoint, sediments were also observed in the corresponding sample based on galactolipid, but to a lesser extent, which could be redispersed to a fine dispersion by gentle agitation.

Example 7

Cytotoxicity Tests

In vitro cytotoxicity assays are valuable for the evaluation of the toxicity of materials, which come into close contact with living tissues.

Selected formulations were tested for in vitro cytotoxicity in cultured mammalian cells (L 929 mouse fibroblasts). The test design was based on the US Pharmacopeia 26th edition, Method <87> and the ISO 10993-5 standard.

Formulations D and E (see Example 4, Table 2) were mixed with complete cell culture medium (HAM F12 medium with 10% foetal bovine serum) at concentrations of 10, 2, 0.4 and 0.08% (v/v). These test solutions were used to treat triplicate cell cultures for 24 h. Triplicate untreated cultures, negative controls (treated with an extract of polypropylene) and positive controls (treated with an extract of tin-stabilised polyvinyl chloride) were included.

Both formulations showed no to slight toxicity (cytotoxicity grade 0-1) when tested at 10% (v/v) and no toxicity (cytotoxicity grade 0) at 2%, 0.4% and 0.08% (v/v).

Cytotoxicity test with a positive control solution containing 100 ppm LL-37 in PBS caused mild toxicity (cytotoxicity grade 2) at all four concentrations tested (10, 2, 0.4 and 0.08% mixtures of the solution with cell culture medium). This level of toxicity is defined as 20-50% of the cells being dead or showing morphological signs of toxicity. The scale has a range of 0 to 4 and when test extracts of medical devices are tested, grades 3 and 4 fail the test. This positive control solution is considerably more toxic than formulation D and E which showed no or just slight toxicity.

BIOLOGICAL EXPERIMENTS

Based on our recent findings that
hCAP18/LL-37 is induced in skin and mucous membranes in association with inflammation and wounding, and
hCAP18/LL-37 is lacking in chronic ulcer epithelium despite massive inflammation,
we hypothesized that hCAP18/LL-37 is involved in the regenerative capacity of skin epithelium. The following experiments were performed to test this hypothesis.

Test 1

Investigation of the Expression Pattern of hCAP18/LL-37 in Non-Inflammatory Human Wound Healing Tissue Samples Human skin was obtained from routine abdominal or breast reduction surgery. Under sterile conditions, full-thickness wounds were made, on the epidermal side, with a 3-mm biopsy punch. These ex vivo wounds were excised with a 6-mm biopsy punch and subsequently transferred to 24-well plates and covered with 2 ml of medium. Such wounds reproducibly re-epithelialize within 4-7 days (Kratz et al. *Scand J Plast Reconstr Surg Hand Surg* 28:107-112, 1994; Inoue et al., *J Invest Dermatol* 104:479-483, 1995; Kratz et al., *Microsc Res Tech* 42:345-350, 1998). Medium, DMEM (Dulbecco's modified Eagle's medium, GIBCO) containing 10% fetal calf serum (FCS) and antibiotics (PEST=penicillin 50 U/ml and streptomycin 50 mg/ml), was changed every third day. Wounds were harvested at different time-points, by 2, 4 and 7 days post-wounding and snap frozen. In total, the experiment was repeated four times. Four different donors were used and triplicate wounds were made for each condition in every experiment. In each experiment, only skin from a single donor was used.

Preparation of RNA Probes

To detect mRNA for the hCAP18 gene and immunoreactivity for hCAP18/LL-37 we performed in situ hybridization and immunohisto-chemistry on samples of wounds representing all time-points of sequential re-epithelialization. For in situ hybridization we used $^{35}$S-labeled antisense and sense RNA probes and the experiment was performed as described (Frohm Nilsson et al., *Infect Immun* 67:2561-2566, 1999).

Preparation of LL-37 Antibody

For immunohistochemistry we raised and prepared a polyclonal LL-37 antibody as follows: LL-37 peptide (lot YS 5253, EuroDiagnostica AB, Malmö, Sweden) was prepared as a trifluoroacetate salt according to Fmoc-strategy using solid phase synthesis (Fields and Noble, 1990) and purified by HPLC to a purity of 98%. Biological activity of the peptide was confirmed in an antibacterial assay. The peptide was used for immunization of three rabbits according to a standard protocol (AgriSera, Vännäs, Sweden). Polyclonal antiserum was affinity-purified using synthetic LL-37 peptide and the purified antiserum was assessed with ELISA. IgG concentration of the immune serum was diluted to 0.5 mg/ml. Pre-immune serum was collected from each rabbit and the IgG concentration was 2 mg/ml.

Immunohistochemistry

All biopsies were snap frozen and handled identically. In short, 6-7 µm thick cryostat sections were incubated with the LL-37 antibody at dilutions 1:1000 and 1:2000 and stained according to the indirect peroxidase method using a Vectastain kit (Vector Laboratories, Burlingame, USA) and following the manufacturer's instructions. Sections were counterstained with Mayer's hematoxyline solution. All experiments were repeated minimum three times to ensure reproducability. As controls, serial tissue sections were processed in parallel without adding primary antibody and using pre-immune rabbit IgG (DAKO, Glostrup, Denmark) as primary antibody.

Results

At time-point 0 h there was moderate expression of hCAP18 mRNA and LL-37 protein in the basal layer of the epidermis throughout the tissue consistent with our previous findings of a constitutive hCAP18 expression in basal epidermis. Wounds harvested at different time-points during re-epithelialization demonstrated a distinct signal for hCAP 18 mRNA and LL-37 protein in the epithelium migrating to cover the wounded surface. No cells in the underlying dermal matrix were positive for hCAP18/LL-37. These results indicate that de novo synthesis of hCAP 18 occurs in keratinocytes during re-epithelialization without inflammation and support our hypothesis that hCAP 18 may be linked to epithelial regeneration.

Test 2

Inhibition of Re-Epithelializing of Human Skin Wounds Ex Vivo with LL-37 Antibody LL-37 antibody, prepared in Test 1, was added in 2 ml medium per well (DMEM, +10% FCS and PEST) to a final antibody dilution of 1:10, 1:100 and 1:1000. As control we used the corresponding pre-immune serum at a final IgG concentration equal to the 1:10 dilution of the LL-37 antiserum and a set of wounds treated only with medium. Each experimental condition was made in triplicates and repeated twice. The media were changed every third day and LL-37 antibody or pre-immune serum was added as described above. The ex vivo wounds were harvested 2, 4 and 7 days post-wounding. All specimens were snap frozen, sectioned in completion and mounted on Superfrost Plus slides prior to staining with hematoxylin-eosine. Sections representing maximal re-epithelialization in the center of the wounds were selected for evaluation. The proliferative capacity of keratinocytes was investigated through immunohisto-chemistry with the proliferation marker Ki67 (mouse monoclonal Ki67 antiserum (DAKO, Glostrup, Denmark) at 1:25 dilution) in wounds representing all treatment conditions.

Results

Treatment with LL-37 antibody produced a concentration-dependant inhibition of re-epithelialization. All wounds treated with the highest LL-37 antibody concentration (1:10) failed to re-epithelialize. In these wounds only single keratinocytes with a fragile flattened appearance had migrated from each wound edge. The wounds treated with LL-37 at medium concentration (1:100) showed delayed re-epithelialization, these wounds were mostly healed by day 7 but not by day 4. Moreover, the epithelium was thinner and the keratinocytes had a fragile appearance. Wounds treated with LL-37 antibody at the lowest concentration (1:1000) did not differ from control wounds, which had all healed by day 4 with a 2-3 layer robust epithelium. Control wounds treated with only medium and control IgG antibody healed equally. In the control wounds the majority of cells in the re-epithelializing tongue were positive for the proliferation marker Ki67, whereas there were no Ki67 positive cells in the wounds treated with LL-37 at 1:10. We concluded from this experiment that LL-37 may be critically involved in skin re-epithelialization and that the proliferative capacity seemed preferentially affected, since blocking with LL-37 antibody allowed the initial migration of single cells from the wound edge, but effectively prevented further proliferation of the keratinocytes.

Test 3

Proliferation of HaCat Cells by Treatment with Synthetic, Biologically Active LL-37 Peptide Per Se and in Combination with a Polar Lipid Carrier HaCat cells were used for these experiments. HaCat cells are an immortalized human keratinocyte cell line (Boukamp et al., *J Cell Biol* 106:761-771, 1988), which is suitable for experimental keratinocyte research. HaCat cells were cultured in medium (DMEM, +10% FCS and PEST). Both types of cell cultures were treated with synthetic, bioactive LL-37 (lot YS 5253). In addition a mixture of LL-37 (114 µg/ml) and CPL-Galactolipid (0.2%) in medium containing serum at either 2 or 10% was added to evaluate the capacity to increase proliferation and inhibit cytotoxicity. Cells were harvested at different time-points (24 h, 48 h, 72 h and 96 h) and counted by flowcytometry (Becton-Dickinson) and stained by Trypan-Blue to evaluate viability. Positivity for Trypan-Blue indicates that the cell membrane has been damaged. Proliferation and viability were also ascertained by measuring mitochondrial activity (WST-1, Roche, Cook et al. *Anal Biochem* 179:1-7, 1989).

TABLE 6

Proliferation of HaCat Cells at 96 h Assessed by Flowcytometry

| EGF (nM) | LL-37 (µg/ml) | Serum Conc. (%) | Number of Cells (Mean) | Trypan Blue + (%) | Increased Proliferation (%) |
|---|---|---|---|---|---|
| — | — | 10 | 32270 | <1 | 0 |
| 1.7 | — | 10 | 42000 | <1 | 30 |
| — | 25 | 10 | 36470 | <1 | 13 |
| — | 50 | 10 | 40950 | <1 | 27 |
| — | 100 | 10 | 66430 | <1 | 100 |
| — | 25 | 2 | 32130 | <1 | 0 |
| — | 50 | 2 | 53620 | 30-50 | Not relevant Cytotoxic effect |
| — | 100 | 2 | 15120 | 100 | Not relevant Cytotoxic effect |

Increase in cell proliferation is calculated in comparison with baseline (-EGF). Mean values from triplicate samples/condition in three separate experiments are presented

TABLE 7

Proliferation and Viability of HaCat Cells at 48 h Measured by Mitochondrial Activity (WST-1)

| EGF (nM) | LL-37 (µg/ml) | Serum Conc. (%) | Absorbance | Trypan Blue + (%) | Increased Proliferation (%) |
|---|---|---|---|---|---|
| — | — | 10 | 0.622 | <1 | 0 |
| 1.7 | — | 10 | 1.107 | <1 | 77 |
| — | 100 | 10 | 1.110 | <1 | 78 |

Increase in cell proliferation is calculated in comparison with baseline (-EGF). Mean values from 6 samples/condition in one experiment are presented

TABLE 8

Proliferation of HaCat Cells at 72 h Assessed by Flowcytometry

| EGF (nM) | LL-37 (µg/ml) | Lipid (0.2%) | Serum Conc. (%) | Number of Cells (Mean) | Trypan Blue + (%) | Increased Proliferation (%) |
|---|---|---|---|---|---|---|
| — | — | − | 10 | 55207 | <1 | 0 |
| 1.7 | — | − | 10 | 85050 | <1 | 54 |
| 1.7 | — | + | 10 | 87640 | <1 | 58 |
| — | 100 | − | 10 | 88853 | <1 | 61 |
| — | 100 | + | 10 | 91980 | <1 | 66 |
| — | 100 | − | 2 | 150500 | 100 | Not relevant Cytotoxic effect |
| — | 100 | + | 2 | 87360 | <1 | 58 |

Increase in proliferation is calculated in comparson with baseline (-EGF). Mean valued from triplicate samples/condition in one experiment are presented.

Results

The treatment of HaCat cells with LL-37 peptide resulted in a concentration-dependant increase in proliferation. This indicates that LL-37 peptide has the capacity to stimulate the proliferation of keratinocytes to a level that equals or surpasses that of EGF, the golden standard for epithelial cell proliferation. We have used EGF at 1.7 nM since this has been established as optimal to stimulate proliferation of keratinocytes in culture and has become a standard culture condition (Cohen et al., *Dev Biol* 12:394-407, 1965). HaCat cells are highly proliferating epithelial cells and it is interesting that LL-37 can increase the proliferation of these cells even further. The cytotoxic effect induced by LL-37 at 100 µg/ml, in 2% serum was completely abolished when lipid was added to the mixture, indicating that the lipid is able to substitute for serum in this experimental condition.

The test has shown that synthetic, bioactive LL-37 (25-100 µg/ml) added to cell cultures of HaCat cells, in media with 10% Fetal Calf Serum (FCS), increases proliferation in a concentration-dependent manner. However, if the peptide (100 µg/ml) was added to a keratinocyte culture in a medium containing 2% FCS, all of the keratinocytes became positive with Trypan Blue staining, indicating a cytotoxic effect on these cells.

The cytotoxic activity of cathelicidin is inhibited by the presence of serum, a mechanism thought to protect the host cells from potentially harmful effects. Our data confirms that the cytotoxic effect of LL-37 is inhibited in the presence of serum (10%). In addition, the mixture of LL-37 (25 µM) and polar lipid carrier (0.2%), in medium containing the lower serum concentration (2% FCS), inhibits the cytotoxic effect and increases the proliferation. These data suggest that the polar lipid carrier has similar protecting capacity as serum, without interfering with the LL-37 bioactivity.

Primary data show that human keratinocytes are proliferated in the same way as HaCat cells.

Test 4

Proliferation of HaCat Cells by Treatment with the Synthetic Peptides LL-36, LL-37 and LL-38

HaCat cells were cultured in medium (DMEM, +10% FCS and PEST). HaCaT cells were plated in 96 well plates (Falcon, USA) at the concentration of 2000 cells per well. Cells were plated at −48 hours and stimulated with different concen-trations of synthetic LL-37, LL-36, and LL-38 peptide by hour 0 and after 48 hours.

The testing was done in one experiment with 6 wells in each condition. 1 Ci/mmol of $^3$H-Thymidine (THYMIDINE, [METHYL-$^3$H]-740.0 GBq/mmol (20.00 Ci/mmol) 1.0 ml of Ethanol:Water, 7:3, Perkin Elmer Life Sciences Inc. Boston Mass., USA) was added to each well and incubated for 12-17 hours. Proliferation was evaluated by $^3$H-Thymidine incorporation a liquid scintilator (MicroBeta Perkin Elmer Life Sciences Inc. Boston Mass., USA) after 72 and 96 hours.

TABLE 9

Proliferation of HaCat Cells by LL-37 at 96 h Assessed by $^3$H-Thymidine Incorporation after 72 and 96 Hours

| LL-37 (μg/ml) | Serum Conc. (%) | Counts Per Minute (Mean) | Standard Deviation (+/−) | Increased Proliferation (%) |
|---|---|---|---|---|
| 0 | 10 | 52774 | 11639 | 0 |
| 1.00 | 10 | 75445 | 32827 | 43 |
| 5.00 | 10 | 102353 | 33808 | 94 |
| 10.00 | 10 | 73548 | 8424 | 39 |
| 25.00 | 10 | 76510 | 10550 | 45 |
| 50.00 | 10 | 65119 | 8565 | 23 |

Increase in cell proliferation (Proliferation Index) is calculated in comparison with baseline (Control = 0 μg/ml). Mean values from four samples per condition in one experiment are presented.

TABLE 10

HaCat Cells Stimulated by LL-36 Peptide. Proliferation Assessed by 3H-Thymidine Incorporation after 96 Hours

| LL-36 (μg/ml) | Serum Conc. (%) | Counts Per Minute (Mean) | Standard Deviation (+/−) | Increased Proliferation (%) |
|---|---|---|---|---|
| 0 | 10 | 69323 | 7511 | 0 |
| 1.00 | 10 | 86253 | 10770 | 24 |
| 5.00 | 10 | 116381 | 14570 | 68 |
| 10.00 | 10 | 70157 | 3660 | 1 |
| 25.00 | 10 | 72674 | 7965 | 5 |
| 50.00 | 10 | 68560 | 11699 | −1 |

Increase in cell proliferation (Proliferation Index) is calculated in comparison with baseline (Control = 0 μg/ml). Mean values from four samples per condition in one experiment are presented.

TABLE 11

HaCat Cells Stimulated by LL-38 Peptide. Proliferation Assessed by 3H-Thymidine Incorporation after 96 Hours

| LL-38 (μg/ml) | Serum Conc. (%) | Counts Per Minute (Mean) | Standard Deviation (+/−) | Increased Proliferation (%) |
|---|---|---|---|---|
| 0 | 10 | 79191 | 15277 | 0 |
| 1.00 | 10 | 82008 | 7911 | 4 |
| 5.00 | 10 | 68694 | 16599 | −13 |
| 10.00 | 10 | 57293 | 8512 | −28 |
| 25.00 | 10 | 54294 | 14335 | −31 |
| 50.00 | 10 | 48701 | 6080 | −39 |

Increase in cell proliferation (Proliferation Index) is calculated in comparison with baseline (Control = 0 μg/ml). Mean values from four samples per condition in one experiment are presented.

Test 5

Proliferation of Human Fibroblasts by Treatment with LL-37 Peptide

The peptide LL-37 used in this and following tests was as described in Example 1 (lot 971/26). The fibroblasts, a type of stromal cells, were obtained from injured and uninjured skin in patients with chronic leg ulcers due to venous insufficiency. Punch-biopsies (4-mm) were taken from the wound margin including 50% of the epithelialized area and from uninjured skin in the knee region. Individuals with a history of diabetes mellitus, arterial insufficiency or chronic inflammatory disease were excluded. Patients with signs of eczema in the ulcer margin, clinical signs of infection or undergoing systemic or topical antibiotic treatment at the time for biopsy were also excluded. Patients included were all treated with inert local dressings and standard compression bandaging.

Fibroblast were put in culture using explant technique (Hehenberger et al., *Cell Biochem Funct* 15:197-201, 1997). Fibroblasts were plated in 96 well plates (Falcon, USA) at the concentration of 2000 cells per well. Cells were plated at −48 hours and stimulated with different concentrations of synthetic LL-37 peptide by hour 0. The testing was done in one experiment with 6 wells in each condition. Proliferation and viability were ascertained by measuring mitochondrial activity (WST-1, Roche) after 24 h and 48 h. See Table 12 and Table 13 below. Increase in cell proliferation (Proliferation Index) is calculated in comparison with baseline (Control=0 μg/ml). Mean values from six samples per condition in one experiment are presented.

TABLE 12

Human Wound Fibroblast Stimulated by LL-37. Proliferation and Viability of Human Fibroblasts Measured by Mitochondrial Activity (WST-1) at 48 Hours

| LL-37 (μg/ml) | Lipid (0.2%) | Serum Conc. (%) | Absorbance | Standard Deviation (+/−) | Increased Proliferation (%) |
|---|---|---|---|---|---|
| — | − | 10 | 0.785 | 0.020 | 0 |
| 25 | − | 10 | 1.171 | 0.242 | 49 |
| 50 | − | 10 | 1.073 | 0.199 | 37 |
| 100 | − | 10 | 0.955 | 0.187 | 22 |
| 100 | + | 2 | 0.960 | 0.122 | 22 |

TABLE 13

Human Normal Fibroblast Stimulated by LL-37 Peptide. Proliferation and Viability of Human Fibroblasts Measured by Mitochondrial Activity (WST-1) at 48 Hours

| LL-37 (μg/ml) | Serum Conc. (%) | Absorbance | Standard Deviation (+/−) | Increased Proliferation (%) |
|---|---|---|---|---|
| — | 10 | 0.560 | 0.019 | 0 |
| 25 | 10 | 0.597 | 0.067 | 7 |
| 50 | 10 | 0.626 | 0.076 | 12 |
| 100 | 10 | 0.669 | 0.051 | 19 |

Test 6

Transgenic Expression of hCAP18 in HEK293 Cells and Proliferation of HEK293-hCAP18 Cells A Bfa1 fragment from Image clone 3057931 (ref) containing the entire coding sequence for hCAP18 including the 16 bp of the 5'-untranslated region, was subcloned into the SmaI-site of the bycistronic vector pIRES2-EGFP (BD Biosciences, Bedford, Mass.). Human embryonic kidney cells, HEK293, were transfected using Fugene (Roche Diagnostics, Indianapolis, Ind.) under standard conditions, and selected for two weeks with 400 ng/ml G418 antibioticum (Invitrogen, Paisley, UK). The cells were sorted for EGFP expression with a MoFlo® high speed cell sorting flow cytometer (DakoCytomation, Fort Collins, Colo.) using Summit™ software for data analysis, and their expression of CAP18 was quantified by immunoblotting. Control cell lines were similarly established by transfection with the vector only expressing EGFP.

For proliferation assay, cell lines were harvested at 70% confluence and seeded in 24-well plates. After 24 hours, medium was changed and cells were cultured in 2 ml of medium (OPTIMEM, Gibco BRL, Life Technologies, Scotland) supplemented with 5% FCS and PEST. All conditions were performed in triplicates. Medium was changed every second day. Cell lines were then harvested at day 6 and counted by Flow Cytometry. Cell viability was measured with Trypan Blue; under all conditions <5% of the cells were Trypan Blue positive. Increase in cell proliferation (Proliferation Index) is calculated in comparison with baseline (HEK293-EGFP). Mean values from triplicate samples per condition in one experiment are presented.

TABLE 14

Proliferation of HEK293-hCAP-18 Cells at 144 Hours Assessed by Flow-Cytometry

| Cell Type | Serum Conc. (%) | Number of Cells (Mean) | Standard Deviation (+/-) | Increased Proliferation (%) |
|---|---|---|---|---|
| HEK293-EGFP | 5 | 169063 | 63726 | 0 |
| HEK293-hCAP18 | 5 | 485884 | 88168 | 187 |

The proliferation of the HEK293-hCAP18 cells was also assessed by incorporation of $^3$H-thymidine and the results obtained are presented in Table 15 below. The increase in cell proliferation (Proliferation Index) is calculated in comparison with baseline (HEK293-EGFP). Mean values from four samples per condition in one experiment are presented.

TABLE 15

Proliferation of HEK293-hCAP-18 Cells at 144 Hours Assessed by $^3$H-Thymidine Incorporation after 96 Hours

| Cell Type | Serum Conc. (%) | Counts Per Minute (Mean) | Standard Deviation (+/-) | Increased Proliferation (%) |
|---|---|---|---|---|
| HEK293-EGFP | 0.1 | 364 | 118 | 0 |
| HEK293-hCAP18 | 0.1 | 796 | 206 | 111 |
| HEK293-EGFP | 0.5 | 811 | 459 | 0 |
| HEK293-hCAP18 | 0.5 | 2271 | 792 | 180 |
| HEK293-EGFP | 1 | 744 | 433 | 0 |
| HEK293-hCAP18 | 1 | 2303 | 359 | 209 |
| HEK293-EGFP | 2 | 767 | 334 | 0 |
| HEK293-hCAP18 | 2 | 3483 | 771 | 354 |
| HEK293-EGFP | 5 | 958 | 414 | 0 |
| HEK293-hCAP18 | 5 | 6088 | 1783 | 534 |
| HEK293-EGFP | 10 | 1806 | 664 | 0 |
| HEK293-hCAP18 | 10 | 6541 | 2827 | 262 |

Test 7

Culturing of Human Cells for Transplantation in Different Growth Media

Culture of Epithelial Cells

A piece of skin, 1×1 cm, is excised from healthy skin of the patient. The skin is minced and treated with trypsin/EDTA (0.05/0.01%) and 2-5×10$^6$ of the recruited keratinocytes are added to 1.5×10$^6$ mitomycin-pretreated (4 µg/ml, 2 h) 3T3 cells in 75 cm$^2$ culture flasks. Growth medium A containing LL-37 peptide is added. Cells are harvested by trypsination as sheets and transplanted onto the patient.

Growth Medium A is used for culture of epithelial cells such as e.g. keratinocytes in vitro and consists of Basal Medium and a growth promoting kit (GPK) including a) LL-37 peptide in a salt solution, b) penicillin+streptomycin, c) insulin, d) transferring, e) triiodotyronine, f) hydrocortisone, g) choleratoxin, and a selected cytoxicity reducing agent, such as serum or a polar lipid.

Culture of Stromal Cells

Stromal cells are obtained from a 4 mm skin biopsy, cleaned from subcutaneous tissue and plated in cell culture dishes using the explant technique to obtain primary fibroblasts. Growth medium B is used for culturing the biopsy. Cells are harvested by trypsination and given back to the patient.

Growth Medium B is used for culture of stromal cells such as e.g. fibroblasts in vitro and consists of Basal medium and a growth promoting kit including a) LL-37 peptide in a salt solution, b) penicillin+streptomycin, and a selected cytotoxicity reducing agent, such as serum or a polar lipid.

Basal medium is based on double-distilled water containing inorganic salts, phenol red, glucose, thymidine, hypoxanthinine, HEPES, sodium pyruvate, aminopterin, amino acids and vitamins

SUMMARY OF THE EXPERIMENTS

In summary, it has been demonstrated that LL-37 is produced in skin epithelium during normal wound healing and that LL-37 is required for re-epithelializa-tion to occur. We have also shown that endogenous LL-37 is lacking in chronic ulcer epithelium. We therefore propose that treatment with LL-37, as well as with N-terminal fragments of said peptide, and functional derivates thereof provides a rational strategy to promote healing of such ulcers. Furthermore, addition of LL-37 and transgenic expression of hCAP18/LL-37 also stimulates proliferation of healthy cells indicating that LL-37 can be used to enhance both normal and deficient epithelial repair in vivo and proliferation of epithelial cells in vitro for autologous cell transplantation. We have also identified a suitable carrier and delivery system that reduces cytotoxicity and has the potential to protect from rapid degradation in vivo of LL-37 and other cathelicidin peptides.

The invention claimed is:

1. A method for the treatment of chronic leg ulcers due to venous insufficiency, comprising administering a peptide LL-37 (SEQ ID NO: 1) or a pharmaceutically acceptable salt thereof to a subject in need of such treatment.

2. The mother accord to claim 1, wherein said peptide LL-37 is in the form of an acetate salt.

* * * * *

SEQUENCE LISTING

<160> NUMBER OF SEQ ID NOS: 21

<210> SEQ ID NO 1
<211> LENGTH: 37
<212> TYPE: PRT
<213> ORGANISM: Homo sapiens
<220> FEATURE:
<221> NAME/KEY: PEPTIDE
<222> LOCATION: (1)..(37)
<223> OTHER INFORMATION: LL-37

<400> SEQUENCE: 1

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 2
<211> LENGTH: 36
<212> TYPE: PRT
<213> ORGANISM: Artificial Sequence
<220> FEATURE:
<223> OTHER INFORMATION: Synthetic Peptide LL-36

<400> SEQUENCE: 2

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu
        35

<210> SEQ ID NO 3
<211> LENGTH: 35
<212> TYPE: PRT
<213> ORGANISM: Artificial Sequence
<220> FEATURE:
<223> OTHER INFORMATION: Synthetic Peptide LL-35

<400> SEQUENCE: 3

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr
        35

<210> SEQ ID NO 4
<211> LENGTH: 34
<212> TYPE: PRT
<213> ORGANISM: Artificial Sequence
<220> FEATURE:
<223> OTHER INFORMATION: Synthetic Peptide LL-34

<400> SEQUENCE: 4

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg

<210> SEQ ID NO 5
<211> LENGTH: 33
<212> TYPE: PRT
<213> ORGANISM: Artificial Sequence
<220> FEATURE:
<223> OTHER INFORMATION: Synthetic Peptide LL-33

<400> SEQUENCE: 5

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro

<210> SEQ ID NO 6
<211> LENGTH: 32
<212> TYPE: PRT
<213> ORGANISM: Artificial Sequence
<220> FEATURE:
<223> OTHER INFORMATION: Synthetic Peptide LL-32

<400> SEQUENCE: 6

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: Synthetic Peptide LL-31

<400> SEQUENCE: 7

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Synthetic Peptide LL-30

<400> SEQUENCE: 8

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn
            20                  25                  30

<210> SEQ ID NO 9
<211> LENGTH: 29
<212> TYPE: PRT
<213> ORGANISM: Artificial Sequence
<220> FEATURE:
<223> OTHER INFORMATION: Synthetic Peptide LL-29

<400> SEQUENCE: 9

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg
            20                  25

<210> SEQ ID NO 10
<211> LENGTH: 28
<212> TYPE: PRT
<213> ORGANISM: Artificial
<220> FEATURE:
<223> OTHER INFORMATION: Synthetic Peptide LL-28

<400> SEQUENCE: 10

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu
            20                  25

<210> SEQ ID NO 11
<211> LENGTH: 27
<212> TYPE: PRT
<213> ORGANISM: Artificial Sequence
<220> FEATURE:
<223> OTHER INFORMATION: Synthetic Peptide LL-27

<400> SEQUENCE: 11

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe
            20                  25

<210> SEQ ID NO 12
<211> LENGTH: 26
<212> TYPE: PRT
<213> ORGANISM: Artificial Sequence
<220> FEATURE:
<223> OTHER INFORMATION: Synthetic Peptide LL-26

<400> SEQUENCE: 12

Leu Leu Gly Asp Phe Phe Arg Lys Ser Lys Glu Lys Ile Gly Lys Glu
1               5                   10                  15

Phe Lys Arg Ile Val Gln Arg Ile Lys Asp
            20                  25

<210> SEQ ID NO 13
<211> LENGTH: 25
<212> TYPE: PRT
<213> ORGANISM: Artificial Sequence
<220> FEATURE:
<223> OTHER INFORMATION: Synthetic Peptide LL-25

<400> SEQUENCE: 13

Leu Leu Gly Asp Phe Phe Arg Lys Ser Lys Glu Lys Ile Gly Lys Glu
1               5                   10                  15

Phe Lys Arg Ile Val Gln Arg Ile Lys
            20                  25

<210> SEQ ID NO 14
<211> LENGTH: 24
<212> TYPE: PRT
<213> ORGANISM: Artificial Sequence
<220> FEATURE:
<223> OTHER INFORMATION: Synthetic Peptide LL-24

<400> SEQUENCE: 14

Leu Leu Gly Asp Phe Phe Arg Lys Ser Lys Glu Lys Ile Gly Lys Glu
1               5                   10                  15

```
Phe Lys Arg Ile Val Gln Arg Ile
            20

<210> SEQ ID NO 15
<211> LENGTH: 23
<212> TYPE: PRT
<213> ORGANISM: Artificial Sequence
<220> FEATURE:
<223> OTHER INFORMATION: Synthetic Peptide LL-23

<400> SEQUENCE: 15

Leu Leu Gly Asp Phe Phe Arg Lys Ser Lys Glu Lys Ile Gly Lys Glu
1               5                   10                  15

Phe Lys Arg Ile Val Gln Arg
            20

<210> SEQ ID NO 16
<211> LENGTH: 22
<212> TYPE: PRT
<213> ORGANISM: Artificial Sequence
<220> FEATURE:
<223> OTHER INFORMATION: Synthetic Peptide LL-22

<400> SEQUENCE: 16

Leu Leu Gly Asp Phe Phe Arg Lys Ser Lys Glu Lys Ile Gly Lys Glu
1               5                   10                  15

Phe Lys Arg Ile Val Gln
            20

<210> SEQ ID NO 17
<211> LENGTH: 21
<212> TYPE: PRT
<213> ORGANISM: Artificial Sequence
<220> FEATURE:
<223> OTHER INFORMATION: Synthetic Peptide LL-21

<400> SEQUENCE: 17

Leu Leu Gly Asp Phe Phe Arg Lys Ser Lys Glu Lys Ile Gly Lys Glu
1               5                   10                  15

Phe Lys Arg Ile Val
            20

<210> SEQ ID NO 18
<211> LENGTH: 20
<212> TYPE: PRT
<213> ORGANISM: Artificial Sequence
<220> FEATURE:
<223> OTHER INFORMATION: Synthetic Peptide LL-20

<400> SEQUENCE: 18

Leu Leu Gly Asp Phe Phe Arg Lys Ser Lys Glu Lys Ile Gly Lys Glu
1               5                   10                  15

Phe Lys Arg Ile
            20

<210> SEQ ID NO 19
<211> LENGTH: 38
<212> TYPE: PRT
<213> ORGANISM: Artificial Sequence
<220> FEATURE:
<223> OTHER INFORMATION: Synthetic Peptide LL-38

<400> SEQUENCE: 19

Leu Leu Gly Asp Phe Phe Arg Lys Ser Lys Glu Lys Ile Gly Lys Glu
```

Phe Lys Arg Ile Val Gln Arg Ile Lys Asp Phe Leu Arg Asn Leu Val
1               5                   10                  15

Pro Arg Thr Glu Ser Ser
            20

```
<210> SEQ ID NO 20
<211> LENGTH: 536
<212> TYPE: DNA
<213> ORGANISM: Homo sapiens
<220> FEATURE:
<221> NAME/KEY: misc_feature
<222> LOCATION: (1)..(536)
<223> OTHER INFORMATION: cDNA sequence of the part of the hCAP18 gene
      inserted into the pI RES2-EGFP vector

<400> SEQUENCE: 20
tagagggagg cagacatggg gaccatgaag acccaaaggg atggccactc cctggggcgg    60
tggtcactgg tgctcctgct gctgggcctg gtgatgcctc tggccatcat tgcccaggtc   120
ctcagctaca aggaagctgt gcttcgtgct atagatggca tcaaccagcg gtcctcggat   180
gctaacctct accgcctcct ggacctggac cccaggccca cgatggatgg gacccagac   240 acgccaaagc ctgtgagctt cacagtgaag gagacagtgt gccccaggac gacacagcag   300
tcaccagagg attgtgactt caagaaggac gggctggtga agcggtgtat ggggacagtg   360
accctcaacc aggccagggg ctcctttgac atcagttgtg ataaggataa caagagattt   420
gccctgctgg gtgatttctt ccggaaatct aagagaaga ttggcaaaga gtttaaaaga   480
attgtccaga gaatcaagga ttttttgcgg aatcttgtac caggacaga gtccta      536

<210> SEQ ID NO 21
<211> LENGTH: 5844
<212> TYPE: DNA
<213> ORGANISM: Artificial Sequence
<220> FEATURE:
<223> OTHER INFORMATION: Vector pIRES2-EGFP including the coding
      sequence for hCAP18
<220> FEATURE:
<221> NAME/KEY: misc_feature
<222> LOCATION: (889)..(889)
<223> OTHER INFORMATION: n is a, c, g, or t

<400> SEQUENCE: 21
tagttattaa tagtaatcaa ttacggggtc attagttcat agcccatata tggagttccg    60
cgttacataa cttacggtaa atggcccgcc tggctgaccg cccaacgacc cccgcccatt   120
gacgtcaata atgacgtatg ttcccatagt aacgccaata gggactttcc attgacgtca   180
atgggtggag tatttacggt aaactgccca cttggcagta catcaagtgt atcatatgcc   240
aagtacgccc cctattgacg tcaatgacgg taaatggccc gcctggcatt atgcccagta   300
catgacctta tgggactttc ctacttggca gtacatctac gtattagtca tcgctattac   360
catggtgatg cggttttggc agtacatcaa tgggcgtgga tagcggtttg actcacgggg   420
atttccaagt ctccacccca ttgacgtcaa tgggagtttg ttttggcacc aaaatcaacg   480
ggactttcca aaatgtcgta caactccgcc ccattgacg caaatgggcg gtaggcgtgt   540
acggtgggag gtctatataa gcagagctgg tttagtgaac cgtcagatcc gctagcgcta   600
ccggactcag atctcgagct caagcttcga attctgcagt cgacggtacc gcgggccta   660 gagggaggca gacatgggga ccatgaagac ccaaggggat ggccactccc tggggcggtg   720
gtcactggtg ctcctgctgc tgggcctggt gatgcctctg ccatcattg cccaggtcct   780
```

```
cagctacaag gaagctgtgc ttcgtgctat agatggcatc aaccagcggt cctcggatgc      840
taacctctac cgcctcctgg acctggaccc caggcccacg atggatggng acccagacac      900
gccaaagcct gtgagcttca cagtgaagga cacagtgtgc cccaggacga cacagcagtc      960
accagaggat tgtgacttca agaaggacgg gctggtgaag cggtgtatgg ggacagtgac     1020
cctcaaccag gccagggggct cctttgacat cagttgtgat aaggataaca agagatttgc    1080
cctgctgggt gatttcttcc ggaaatctaa agagaagatt ggcaaagagt ttaaaagaat     1140
tgtccagaga atcaaggatt ttttgcggaa tcttgtaccc aggacagagt cctagggatc     1200
cgcccctctc cctcccccccc ccctaacgtt actggccgaa gccgcttgga ataaggccgg     1260
tgtgcgtttg tctatatgtt attttccacc atattgccgt cttttggcaa tgtgagggcc     1320
cggaaacctg gccctgtctt cttgacgagc attcctaggg gtctttcccc tctcgccaaa     1380
ggaatgcaag gtctgttgaa tgtcgtgaag gaagcagttc ctctggaagc ttcttgaaga     1440
caaacaacgt ctgtagcgac cctttgcagg cagcggaacc ccccacctgg cgacaggtgc     1500
ctctgcggcc aaaagccacg tgtataagat acacctgcaa aggcggcaca accccagtgc     1560
cacgttgtga gttggatagt tgtggaaaga gtcaaatggc tctcctcaag cgtattcaac     1620
aaggggctga aggatgccca aaggtacccc cattgtatgg gatctgatct ggggcctcgg     1680
tgcacatgct ttacatgtgt ttagtcgagg ttaaaaaaac gtctaggccc ccgaaccac      1740 ggggacgtgg ttttcctttg aaaaacacga tgataatatg gccacaacca tggtgagcaa     1800
gggcgaggag ctgttcaccg gggtggtgcc catcctggtc gagctggacg gcgacgtaaa     1860
cggccacaag ttcagcgtgt ccggcgaggg cgagggcgat gccacctacg gcaagctgac     1920
cctgaagttc atctgcacca ccggcaagct gcccgtgccc tggcccaccc tcgtgaccac     1980
cctgacctac ggcgtgcagt gcttcagccg ctaccccgac cacatgaagc agcacgactt     2040
cttcaagtcc gccatgcccg aaggctacgt ccaggagcgc accatcttct tcaaggacga     2100
cggcaactac aagacccgcg ccgaggtgaa gttcgagggc gacaccctgg tgaaccgcat     2160
cgagctgaag ggcatcgact tcaaggagga cggcaacatc ctggggcaca agctggagta     2220
caactacaac agccacaacg tctatatcat ggccgacaag cagaagaacg gcatcaaggt     2280
gaacttcaag atccgccaca acatcgagga cggcagcgtg cagctcgccg accactacca     2340
gcagaacacc cccatcggcg acggccccgt gctgctgccc gacaaccact acctgagcac     2400
ccagtccgcc ctgagcaaag accccaacga gaagcgcgat cacatggtcc tgctggagtt     2460
cgtgaccgcc gccgggatca ctctcggcat ggacgagctg tacaagtaaa gcggccgcga     2520
ctctagatca taatcagcca taccacattt gtagaggttt tacttgcttt aaaaaacctc     2580
ccacacctcc ccctgaacct gaaacataaa atgaatgcaa ttgttgttgt aacttgtttt     2640
attgcagctt ataatggtta caaataaagc aatagcatca caaatttcac aaataaagca     2700
tttttttcac tgcattctag ttgtggtttg tccaaactca tcaatgtatc ttaaggcgta     2760
aattgtaagc gttaatattt tgttaaaatt cgcgttaaat ttttgttaaa tcagctcatt     2820
ttttaaccaa taggccgaaa tcggcaaaat cccttataaa tcaaagaat agaccgagat      2880 agggttgagt gttgttccag tttggaacaa gagtccacta ttaaagaacg tggactccaa     2940
cgtcaaaggg cgaaaaaccg tctatcaggg cgatggccca ctacgtgaac catcacccta     3000
atcaagtttt tgggggtcga ggtgccgtaa agcactaaat cggaacccta agggagccc     3060 ccgatttaga gcttgacggg gaagccggc gaacgtggcg agaaaggaag ggaagaaagc     3120
```

```
gaaaggagcg gcgctaggg cgctggcaag tgtagcggtc acgctgcgcg taaccaccac  3180
acccgccgcg cttaatgcgc cgctacaggg cgcgtcaggt ggcactttc ggggaaatgt  3240
gcgcggaacc cctatttgtt tatttttcta aatacattca aatatgtatc cgctcatgag  3300
acaataaccc tgataaatgc ttcaataata ttgaaaaagg aagagtcctg aggcggaaag  3360
aaccagctgt ggaatgtgtg tcagttaggg tgtggaaagt ccccaggctc cccagcaggc  3420
agaagtatgc aaagcatgca tctcaattag tcagcaacca ggtgtggaaa gtccccaggc  3480
tccccagcag gcagaagtat gcaaagcatg catctcaatt agtcagcaac catagtcccg  3540
cccctaactc cgcccatccc gcccctaact ccgcccagtt ccgcccattc tccgccccat  3600
ggctgactaa ttttttttat ttatgcagag gccgaggccg cctcggcctc tgagctattc  3660
cagaagtagt gaggaggctt ttttggaggc ctaggctttt gcaaagatcg atcaagagac  3720
aggatgagga tcgtttcgca tgattgaaca agatggattg cacgcaggtt ctccggccgc  3780
ttgggtggag aggctattcg gctatgactg ggcacaacag acaatcggct gctctgatgc  3840
cgccgtgttc cggctgtcag cgcaggggcg cccggttctt tttgtcaaga ccgacctgtc  3900
cggtgccctg aatgaactgc aagacgaggc agcgcggcta tcgtggctgg ccacgacggg  3960
cgttccttgc gcagctgtgc tcgacgttgt cactgaagcg ggaagggact ggctgctatt  4020
gggcgaagtg ccggggcagg atctcctgtc atctcacctt gctcctgccg agaaagtatc  4080
catcatggct gatgcaatgc ggcggctgca tacgcttgat ccggctacct gcccattcga  4140
ccaccaagcg aaacatcgca tcgagcgagc acgtactcgg atggaagccg gtcttgtcga  4200
tcaggatgat ctggacgaag agcatcaggg gctcgcgcca gccgaactgt tcgccaggct  4260
caaggcgagc atgcccgacg gcgaggatct cgtcgtgacc catggcgatg cctgcttgcc  4320
gaatatcatg gtggaaaatg gccgcttttc tggattcatc gactgtggcc ggctgggtgt  4380
ggcggaccgc tatcaggaca tagcgttggc tacccgtgat attgctgaag agcttggcgg  4440
cgaatgggct gaccgcttcc tcgtgcttta cggtatcgcc gctcccgatt cgcagcgcat  4500
cgccttctat cgccttcttg acgagttctt ctgagcggga ctctggggtt cgaaatgacc  4560
gaccaagcga cgcccaacct gccatcacga gatttcgatt ccaccgccgc cttctatgaa  4620
aggttgggct tcggaatcgt tttccgggac gccggctgga tgatcctcca gcgcgggat  4680
ctcatgctgg agttcttcgc ccaccctagg gggaggctaa ctgaaacacg aaggagaca  4740
ataccggaag gaacccgcgc tatgacggca ataaaaagac agaataaaac gcacggtgtt  4800
gggtcgtttg ttcataaacg cggggttcgg tcccagggct ggcactctgt cgataccca  4860
ccgagacccc attggggcca atacgcccgc gtttcttcct ttttcccacc ccacccccca  4920
agttcgggtg aaggcccagg gctcgcagcc aacgtcgggg cggcaggccc tgccatagcc  4980
tcaggttact catatatact ttagattgat ttaaaacttc atttttaatt taaaaggatc  5040
taggtgaaga tccttttttga taatctcatg accaaaatcc cttaacgtga gttttcgttc  5100
cactgagcgt cagaccccgt agaaaagatc aaaggatctt cttgagatcc ttttttttctg  5160
cgcgtaatct gctgcttgca acaaaaaaa ccaccgctac cagcggtggt ttgtttgccg  5220
gatcaagagc taccaactct ttttccgaag gtaactggct tcagcagagc gcagatacca  5280
aatactgtcc ttctagtgta gccgtagtta ggccaccact tcaagaactc tgtagcaccg  5340
cctacatacc tcgctctgct aatcctgtta ccagtggctg ctgccagtgg cgataagtcg  5400
tgtcttaccg ggttggactc aagacgatag ttaccggata aggcgcagcg gtcgggctga  5460
acggggggtt cgtgcacaca gcccagcttg gagcgaacga cctacaccga actgagatac  5520
```

```
ctacagcgtg agctatgaga aagcgccacg cttcccgaag ggagaaaggc ggacaggtat    5580
ccggtaagcg gcagggtcgg aacaggagag cgcacgaggg agcttccagg gggaaacgcc    5640
tggtatcttt atagtcctgt cgggtttcgc cacctctgac ttgagcgtcg atttttgtga    5700
tgctcgtcag gggggcggag cctatggaaa aacgccagca acgcggcctt tttacggttc    5760
ctggcctttt gctggccttt tgctcacatg ttctttcctg cgttatcccc tgattctgtg    5820
gataaccgta ttaccgccat gcat                                           5844
```